(12) United States Patent
Simmons et al.

(10) Patent No.: US 12,667,633 B2
(45) Date of Patent: *Jun. 30, 2026

(54) AQUEOUS OZONE FLOOR DISINFECTION SYSTEM

(71) Applicant: BioSure North America LLC, Fair Oaks Ranch, TX (US)

(72) Inventors: Darren Simmons, Fair Oaks Ranch, TX (US); Jeffrey R. Foote, Milton, GA (US); Christopher Salaski, Peachtree City, GA (US); Ivor J.J. Longo, Atlanta, TX (US); Wayne Simmons, Adkins, TX (US); H. Brock Kolls, Alpharetta, GA (US)

(73) Assignee: BioSure North America LLC, Fair Oaks Ranch, TX (US)

( * ) Notice: Subject to any disclaimer, the term of this patent is extended or adjusted under 35 U.S.C. 154(b) by 48 days.

This patent is subject to a terminal disclaimer.

(21) Appl. No.: 18/646,394

(22) Filed: Apr. 25, 2024

(65) Prior Publication Data

US 2025/0177589 A1 Jun. 5, 2025

Related U.S. Application Data

(63) Continuation-in-part of application No. 18/528,194, filed on Dec. 4, 2023, now Pat. No. 12,036,331, and
(Continued)

(51) Int. Cl.
*A61L 2/183* (2026.01)
*A47L 11/40* (2006.01)
(Continued)

(52) U.S. Cl.
CPC ........... *A61L 2/183* (2013.01); *A47L 11/4011* (2013.01); *A47L 11/4083* (2013.01);
(Continued)

(58) Field of Classification Search
CPC .............. A47L 11/4011; A47L 11/4083; A47L 11/4088; A47L 11/00; A61L 2/183;
(Continued)

(56) References Cited

U.S. PATENT DOCUMENTS

| | | | |
|---|---|---|---|
| 11,975,118 B1 * | 5/2024 | Simmons | A61L 2/183 |
| 12,036,331 B1 * | 7/2024 | Simmons | A61L 2/183 |
| 2013/0091653 A1 * | 4/2013 | Pollack | A47L 11/283 |
| | | | 15/322 |

FOREIGN PATENT DOCUMENTS

WO WO-2013042144 A1 * 3/2013 .......... A47L 11/4044

* cited by examiner

*Primary Examiner* — Douglas Lee
(74) *Attorney, Agent, or Firm* — H. Brock Kolls

(57) ABSTRACT

The present invention relates to an aqueous ozone floor disinfection system. A floor cleaning machine traverses a floor surface entering a pre-hygienic zone prior to cleaning, cleaning within a midst-hygienic zone for a cleaning period, and moving away from the midst-hygienic zone creating a post-hygienic zone. An aqueous ozone generator receives water and generates an ozonated concentrate liquid. A post-hygienic mixer ratiometrically blends the ozonated concentrate liquid and water to form a post-hygienic ozone disinfection solution having a predetermined post-hygienic ozone treatment concentration. A post-hygienic nozzle spray of the post-hygienic ozone disinfection solution onto the post-hygienic zone portion of the floor surface for at least the post-hygienic treatment time absent agitation or removal by the floor cleaning machine improving disinfection of the floor surface. The service life of the aqueous ozone generator can be tracked and the disinfected floor surface can be GPS geofenced.

20 Claims, 12 Drawing Sheets

Related U.S. Application Data a continuation-in-part of application No. 18/528,162, filed on Dec. 4, 2023, now Pat. No. 11,975,118.

(51) Int. Cl.
      *A61L 2/24*          (2006.01)
      *A61L 101/02*      (2006.01)
      *C02F 1/461*        (2023.01)

(52) U.S. Cl.
      CPC ............. *A47L 11/4088* (2013.01); *A61L 2/24* (2013.01); *C02F 1/46104* (2013.01); *A61L 2101/02* (2020.08); *A61L 2202/11* (2013.01); *A61L 2202/14* (2013.01); *A61L 2202/15* (2013.01); *A61L 2202/17* (2013.01); *C02F 2201/782* (2013.01); *C02F 2303/04* (2013.01)

(58) Field of Classification Search
      CPC .... A61L 2/24; A61L 2101/02; A61L 2202/11; A61L 2202/14; A61L 2202/15; A61L 2202/17; A61L 2202/25
      See application file for complete search history.

Ozone Disinfection Database
900

Alert !!!
11/13/2023
Ozone
PPM Low

| Date | Technician | Equipment | Geofenced Area Disinfected | Ozone PPM Test |
|---|---|---|---|---|
| 11/9/23 | Jeff | Cleaner-01 | Lobby Area – 'A' | 2.0 ppm |
| 11/10/23 | Darren | Cleaner-02 | Wait Room – 'B' | 2.2 ppm |
| 11/10/23 | Wayne | Cleaner-01 | Lobby Area – 'A' | 2.1 ppm |
| 11/11/23 | Chris | Cleaner-01 | Ward 'C' | 2.5 ppm |
| 11/12/23 | Ivor | Cleaner-03 | Lobby Area 'A' | 2.1 ppm |
| 11/13/23 | Brock | Cleaner-02 | Wait Room 'B' | 0.4 ppm !!! |

PPM 602
604
128
132
136
530 302
Aqueous Ozone Generator
Elec. Chem. Generator
516
606
520 Ozone Sensor
818
816
(A)

| Date | Technician | Equipment | Ozone PPM Test |
|------|-----------|-----------|----------------|
| 11/3/21 | Jeff | Cleaner-01 | 3.2 ppm |
| 11/6/21 | Darren | Cleaner-01 | 3.2 ppm |
| 11/10/21 | Wayne | Cleaner-01 | 3.1 ppm |
| ... | ... | ... | ... |
| 1/20/23 | Chris | Cleaner-01 | 2.5 ppm |
| ... | ... | ... | ... |
| 8/2/23 | Ivor | Cleaner-01 | 2.1 ppm |
| 11/13/23 | Brock | Cleaner-01 | 1.9 ppm |

(B)

820

Ozone PPM 822
826
Replacement Notifications
830
832
828
834
824

(C)

Date/Time/Aqueous Ozone Generator Runtime

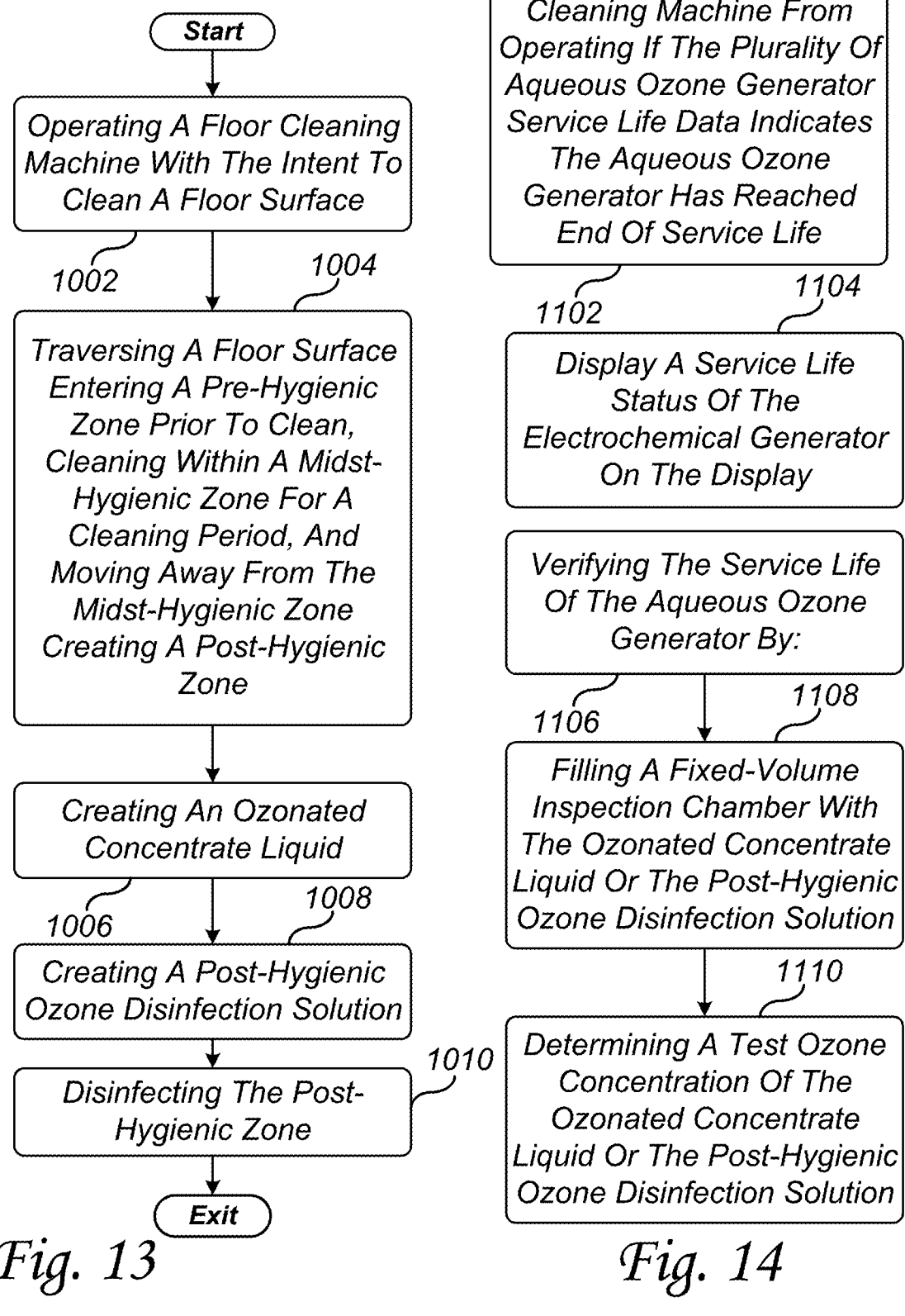

Start

Operating A Floor Cleaning Machine With The Intent To Clean A Floor Surface 1002          1004

Traversing A Floor Surface Entering A Pre-Hygienic Zone Prior To Clean, Cleaning Within A Midst-Hygienic Zone For A Cleaning Period, And Moving Away From The Midst-Hygienic Zone Creating A Post-Hygienic Zone Creating An Ozonated Concentrate Liquid 1006          1008

Creating A Post-Hygienic Ozone Disinfection Solution

1010

Disinfecting The Post-Hygienic Zone

Exit

*Fig. 13*

Preventing The Floor Cleaning Machine From Operating If The Plurality Of Aqueous Ozone Generator Service Life Data Indicates The Aqueous Ozone Generator Has Reached End Of Service Life 1102          1104

Display A Service Life Status Of The Electrochemical Generator On The Display

Verifying The Service Life Of The Aqueous Ozone Generator By:

1106          1108

Filling A Fixed-Volume Inspection Chamber With The Ozonated Concentrate Liquid Or The Post-Hygienic Ozone Disinfection Solution

1110

Determining A Test Ozone Concentration Of The Ozonated Concentrate Liquid Or The Post-Hygienic Ozone Disinfection Solution

*Fig. 14*

Mixing The Post-Hygienic Ozone Disinfection Solution In The Predetermined Post-Hygienic Ozone Treatment Concentration By Transitioning Between:

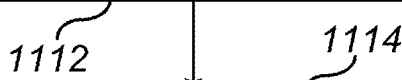

1112          1114

Activating The Water Pump From A Water pulse Width Period

1116

Activating The Concentrate Pump For A Concentrate Pulse Width Period

Recording, By Way Of The GPS, A Disinfected Post-Hygienic Zone GPS Location 1118          1120

Communicating, By Way Of The Communication Interface, The Disinfected Post-Hygienic Zone GPS Location To A Remote Data Processing Resource Dispensing The Post-Hygienic Ozone Disinfection Solution When Motion Of The Floor Cleaning Machine Is Detected

1122

Recording, By Way Of The Ozone Sensor, A Test Ozone Concentration Of The Ozonated Concentrate Liquid Or The Post-Hygienic Ozone Disinfection Soultion 1124          1126

Communicating, By Way Of The Communication Interface, The Test Ozone Concentration A Remote Data Processing Resource

1128

Receiving, From The Remote Data Processing Resource, By Way Of The Communication Interface, A Plurality Of Aqueous Ozone Generator Service Life Data

Fig. 15

AQUEOUS OZONE FLOOR DISINFECTION SYSTEM

CROSS-REFERENCE TO RELATED APPLICATIONS

This application contains subject matter which is related to the subject matter of the following application. The below-listed application is hereby incorporated herein by reference in its entirety:

This is a U.S. non-provisional application that is a continuation in part of a U.S. non-provisional application Ser. No. 18/528,194, inventor Darren Simmons et al., entitled "AQUEOUS OZONE FLOOR DISINFECTION SYSTEM", filed Dec. 4, 2023; and a continuation in part of a U.S. non-provisional application Ser. No. 18/528,162, inventor Darren Simmons et al., entitled "AQUEOUS OZONE FLOOR DISINFECTION SYSTEM", filed Dec. 4, 2023, now U.S. Pat. No. 11,975,118.

TECHNICAL FIELD OF THE INVENTION

This invention relates to an aqueous ozone floor disinfection system. The service lift of the aqueous ozone generator can be tracked and the disinfected floor surface can be GPS geofenced.

BACKGROUND OF THE INVENTION

Before our invention, floor cleaning machines were used to clean floor surfaces. A shortcoming of prior floor cleaning machines is that many use a water and detergent combination that is applied to the floor surface and then vacuumed up. While appearing to clean the surface many prior floor cleaning machines don't disinfect the floor in any meaningful way.

A shortcoming of prior floor cleaning machines that do suggest they disinfect the floor surface do so by applying whichever chemical or disinfection technique in the same location that the cleaning mechanism is currently cleaning, that is trying to clean and disinfect the same spot on the floor at the same time. This approach does a poor job of reliably disinfecting a floor surface.

Another shortcoming of prior floor cleaning machines that suggest they disinfect the floor surface is that the disinfection technology and/or effectiveness can degrade over time. In this regard, perhaps the disinfection worked well at the time of installation and shortly thereafter, but without a way for technicians to validate the performance and/or remotely monitor the system performance the disinfection system can fail to adequately disinfect over much of the time it is in use and no one would know to repair or replace the consumables in the system.

Another shortcoming of prior floor cleaning machines is that the floor areas that have been disinfected are not tracked or mapped so that an organization knows when the disinfection treatment was done and to which floor surface it was applied.

The present invention addresses these and other shortcomings by providing an aqueous ozone floor disinfection system and other advantages. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of an aqueous ozone floor disinfection system that comprises a cleaning mechanism that is capable of traversing a floor surface and cleaning the floor surface, an aqueous ozone generator that receives water and generates an ozonated concentrate liquid from the water, a mixer that receives and ratiometrically blends a portion of the ozonated concentrate liquid with water to form an ozone disinfection solution at a desired ozone concentration level, and a nozzle that sprays the ozone disinfection solution onto the floor surface after it has been cleaned by the cleaning mechanism.

Additional shortcomings of the prior art are overcome and additional advantages are provided through the provision of a method of using an aqueous ozone floor disinfection system. The method comprises the steps of operating a cleaning mechanism on a floor surface and creating an ozonated concentrate liquid from water with an aqueous ozone generator.

The method continues by creating an ozone disinfection solution at a desired concentration level with a mixer that receives and ratiometrically blends a portion of the ozonated concentrate liquid with water, and disinfects the floor surface by spraying the ozone disinfection solution onto the floor surface with a nozzle after it has been cleaned by the cleaning mechanism.

Additional shortcomings of the prior art are overcome and additional advantages are provided through the provision of an aqueous ozone floor disinfection system that comprises a water source, and a floor cleaning machine. The floor cleaning machine comprises a cleaning mechanism. The floor cleaning machine is capable of traversing a floor surface entering a pre-hygienic zone prior to cleaning, cleaning within a midst-hygienic zone for a cleaning period by way of the cleaning mechanism, and moving away from the midst-hygienic zone creating a post-hygienic zone.

The aqueous ozone floor disinfection system further comprises an aqueous ozone generator that receives a portion of the water source and generates from the water source an ozonated concentrate liquid, and a post-hygienic mixer. The post-hygienic mixer receives and ratiometrically blends a portion of the ozonated concentrate liquid and a portion of the water source to form a post-hygienic ozone disinfection solution having a predetermined post-hygienic ozone treatment concentration which is less than the ozone concentration of the ozonated concentrate liquid. The predetermined post-hygienic ozone treatment concentration is selected to achieve sterilization of the floor surface within a post-hygienic treatment time. The post-hygienic treatment time is greater than the cleaning period.

The aqueous ozone floor disinfection system further comprises a post-hygienic nozzle that is mounted on the floor cleaning machine proximate to the transition between the midst-hygienic zone and the post-hygienic zone. The post-hygienic nozzle directs the spray of the post-hygienic ozone disinfection solution onto the post-hygienic zone portion of the floor surface.

In operation, cleaning within the midst-hygienic zone removes debris from the floor surface allowing the post-hygienic ozone disinfection solution sprayed on the post-hygienic zone to contact the floor surface in an unencumbered by debris manner for at least the post-hygienic treatment time absent agitation or removal by the floor cleaning machine improving disinfection of the floor surface.

Additional shortcomings of the prior art are overcome and additional advantages are provided through the provision of an aqueous ozone floor disinfection system that comprises a water source, and a floor cleaning machine. The floor cleaning machine comprises a cleaning mechanism. The floor cleaning machine is capable of traversing a floor surface entering a pre-hygienic zone prior to cleaning, cleaning within a midst-hygienic zone for a cleaning period by way of the cleaning mechanism, and moving away from the midst-hygienic zone creating a post-hygienic zone.

The aqueous ozone floor disinfection system further comprises an aqueous ozone generator that receives a portion of the water source and generates from the water source an ozonated concentrate liquid. The aqueous ozone generator comprises a plumbed housing that is fastened in fluid communication pathways with the water source, the ozonated concentrate liquid, and an electrochemical generator. The electrochemical generator comprises an ion exchange material. The electrochemical generator is interchangeable and removably fastened to the plumbed housing.

The aqueous ozone floor disinfection system further comprises a fixed-volume inspection chamber that receives continuous flow and maintains a fixed-volume portion of the ozonated concentrate liquid or the post-hygienic ozone disinfection solution. The amount of the fixed-volume portion is predetermined by the test requirements of an ozone concentration test implement.

The aqueous ozone floor disinfection system further comprises a post-hygienic mixer that receives and ratiometrically blends a portion of the ozonated concentrate liquid and a portion of the water source to form a post-hygienic ozone disinfection solution having a predetermined post-hygienic ozone treatment concentration which is less than ozone concentration of the ozonated concentrate liquid. The predetermined post-hygienic ozone treatment concentration is selected to achieve sterilization of the floor surface within a post-hygienic treatment time. The post-hygienic treatment time is greater than the cleaning period.

The aqueous ozone floor disinfection system further comprises a post-hygienic nozzle that is mounted on the floor cleaning machine proximate to the transition between the midst-hygienic zone and the post-hygienic zone. The post-hygienic nozzle directs the spray of the post-hygienic ozone disinfection solution onto the post-hygienic zone portion of the floor surface. In operation, cleaning within the midst-hygienic zone removes debris from the floor surface, allowing the post-hygienic ozone disinfection solution sprayed on the post-hygienic zone to contact the floor surface in an unencumbered by debris manner for at least the post-hygienic treatment time absent agitation or removal by the floor cleaning machine improving disinfection of the floor surface.

In operation, the ozone concentration test implement includes at least one of the following: an ozone concentration test strip, an ozone concentration test drop, or an ozone concentration test device. The ozone concentration test implement is manually used by a technician to determine a test ozone concentration of the ozonated concentrate liquid or the post-hygienic ozone disinfection solution within the fixed-volume inspection chamber by inserting the ozone concentration implement into the fixed-volume inspection chamber and then reading the test ozone concentration of ozonated concentrate or the post-hygienic ozone disinfection.

Additional shortcomings of the prior art are overcome and additional advantages are provided through the provision of a method of using an aqueous ozone floor disinfection system. The method comprises the steps of operating a floor cleaning machine with the intent of cleaning a floor surface. The floor cleaning machine comprises a cleaning mechanism.

The method continues by traversing the floor surface, the floor cleaning machine enters a pre-hygienic zone prior to cleaning, cleans within a midst-hygienic zone for a cleaning period by way of the cleaning mechanism, and moves away from the midst-hygienic zone creating a post-hygienic zone.

The method continues by creating an ozonated concentrate liquid. An aqueous ozone generator receives a portion of a water source and generates from the water source the ozonated concentrate liquid.

The method continues by creating a post-hygienic ozone disinfection solution at a predetermined post-hygienic ozone treatment concentration. A post-hygienic mixer receives and ratiometrically blends a portion of the ozonated concentrate liquid and a portion of the water source to form the post-hygienic ozone disinfection solution having the predetermined post-hygienic ozone treatment concentration which is less than ozone concentration of the ozonated concentrate liquid. The predetermined post-hygienic ozone treatment concentration is selected to achieve sterilization of the floor surface within a post-hygienic treatment time. The post-hygienic treatment time is greater than the cleaning period.

The method continues by disinfecting the post-hygienic zone. A post-hygienic nozzle is mounted on the floor cleaning machine proximate to the transition between the midst-hygienic zone and the post-hygienic zone. The post-hygienic nozzle directs the spray of the post-hygienic ozone disinfection solution onto the post-hygienic zone portion of the floor surface. In operation, cleaning within the midst-hygienic zone removes debris from the floor surface allowing the post-hygienic ozone disinfection solution sprayed on the post-hygienic zone to contact the floor surface in an unencumbered by debris manner for at least the post-hygienic treatment time absent agitation or removal by the floor cleaning machine improving disinfection of the floor surface.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 13 illustrates one example of a method of using an aqueous ozone floor disinfection system; and FIGS. 14-15 illustrate exemplary embodiments that can be interchangeably used with the methods of the present invention.

The detailed description explains the preferred embodiments of the invention, together with advantages and features, by way of example with reference to the drawings.

DETAILED DESCRIPTION OF THE INVENTION

Figure 1:
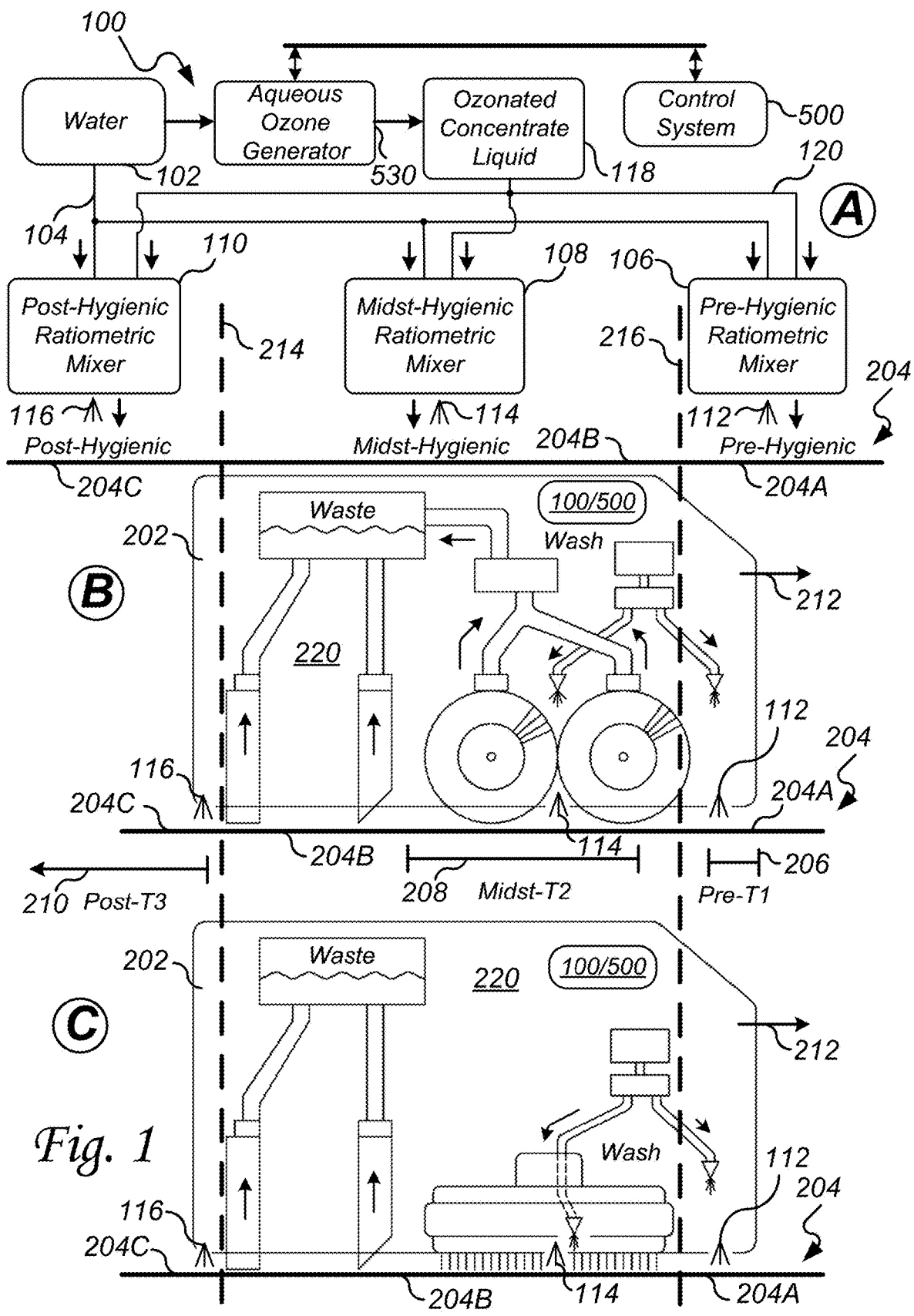
FIG. 1 illustrates one example of an aqueous ozone floor disinfection system.

Turning now to the drawings in greater detail, it will be seen that in FIG. 1 there is illustrated one example of an aqueous ozone ($O_3$) floor disinfection system 100. In an exemplary embodiment, a floor cleaning machine 202 can comprise a cleaning mechanism 220 that can include items such as detergent, brushes, spray nozzles, vacuums, and other items depending on the type or kind of floor cleaning machine.

An advantage, in the present invention, is that aqueous ozone production happens within water and in the absence of air or oxygen gas traditionally used on corona discharge ozone production. The advantage of aqueous ozone is that it forms ozone $O_3$ molecules in large quantities on demand from the water with the help of an ion exchange material. The ozone molecules are produced in high concentration levels and well distributed throughout the water and tend not to break out of the water which makes the aqueous ozone concentration slow to dissipate with a half-life in the range of 20-30 minutes. In this regard, spraying aqueous ozone on a clean floor within the post-hygienic zone 204C and leaving it undistributed by the floor cleaning machine to dry slowly means that the ozone treatment time post-T3 210 can range from many minutes to tens of minutes. It is the long half-life time of aqueous ozone in combination with treating a clean floor surface, within the post-hygienic zone 204C, at sufficient ozone concentration that enables the present invention to reach sterile or near sterile floor surface 204 conditions.

In contrast, corona discharge systems create ozone gas (and a bunch of human-harmful nitrogen species molecules) that then has to be dissolved or dispersed into the water at a low concentration level which easily breaks out of the water and dissipates before any real disinfection benefits can be realized on the floor surface. Additionally, the ozone purity level in aqueous ozone is in the range of 28% whereas corona discharge techniques yield ozone purity in the mid-single digits to low teens with corona discharge in air having lower purity than corona discharge in oxygen.

In operation, floor cleaning machines 202 can move 212 along a floor surface 204, dispense detergents, and use brushes and vacuum to remove debris from the floor surface. In this regard, the floor cleaning machine 202 is capable of traversing the floor surface 204 entering a pre-hygienic zone 204A prior to cleaning, cleaning within a midst-hygienic zone 204B for a cleaning period midst-T2 208 by way of the cleaning mechanism 220, and moving away from the midst-hygienic zone 204B creating a post-hygienic zone 204C.

An advantage in the present invention and with reference to at least FIG. 1, the pre-hygienic zone 204A of floor surface 204 is located just prior to where the floor cleaning machine 202 will clean next as it moves 212 along the floor surface 204. The present invention can ozone disinfection treat each of the three regions with different levels of ozone concentration selected based on the amount of treatment time available. In this regard, within the pre-hygienic zone, there is an ozone disinfection time period referred to as pre-T1 206 created based in part on the speed of the floor cleaning machine 202 in which a floor cleaning machine 202 that is equipped with a pre-hygienic nozzle 112 can spray a pre-hygienic ozone disinfection solution having a predetermined pre-hygienic ozone treatment concentration before the floor cleaning machine 202 will clean the floor surface displacing the pre-hygienic ozone disinfection solution.

Continuing, there is a second ozone disinfection time period referred to as midst-T2 208 created based in part on the speed of the floor cleaning machine 202 in which the floor cleaning machine 202 is actively cleaning the midst-hygienic zone 204B portion of floor surface 204 with detergent, brushes, and other items. If equipped with a midst-hygienic nozzle 114, a midst-hygienic ozone disinfection solution having a predetermined midst-hygienic ozone treatment concentration can be sprayed within the midst-hygienic zone 204B while the floor cleaning machine 202 is cleaning the midst-hygienic zone 204B of the floor surface 204.

Continuing, there is a third ozone disinfection time period referred to as post-T3 210 created as floor cleaning machine 202 moves away from the midst-hygienic zone 204B after cleaning, creating the post-hygienic zone 204C. If equipped with a post-hygienic nozzle 116, a post-hygienic ozone disinfection solution having a predetermined post-hygienic ozone treatment concentration can be sprayed within the post-hygienic zone 204C and left to dry by evaporation. In this regard, with the floor surface 204 cleaned and the debris removed the post-hygienic ozone disinfection solution better contacts the floor surface and since once sprayed on the floor surface 204 remains undisturbed until air dried the contact treatment time post-T3 210 can be lengthy maximizing kill time for bacteria, mold, mildew, and other pathogens resulting in the ability to achieve sterile or near-sterile conditions of the floor surface 204.

An advantage, in the present, is that each of the pre-hygienic ozone disinfection solution sprayed from nozzle 112, midst-hygienic ozone disinfection solution sprayed from nozzle 114, and post-hygienic ozone disinfection solution sprayed from nozzle 116 can be ratiometrically mixed (ratio of water 102 and ozonated concentrate liquid 118) to have different aqueous ozone concentrations ($O_3$ ppm). These different aqueous ozone concentrations are referred to as a predetermined pre-hygienic ozone treatment concentration, a predetermined midst-hygienic ozone treatment concentration, and a predetermined post-hygienic ozone treatment concentration.

In this regard, in an exemplary embodiment, since pre-T1 206, midst-T2 208, and post-T3 210 vary in duration the concentration of the ozone disinfection spray can be selected accordingly with a shorter time period receiving a higher ozone concentration.

In another exemplary embodiment, in addition to variations in floor surface 204 contact duration (pre-T1 206, midst-T2 208, and post-T3 210) the concentration of the ozone disinfection spray can be selected or adjusted based on the starting condition of the floor surface 204 conditions. In this regard, the pre-hygienic zone 204A comprises the floor surface 204 covered by debris, the midst-hygienic zone 204B comprises water, detergent, brush agitation, and debris, and the post-hygienic zone 204C comprises only the clean floor surface 204.

In another exemplary embodiment, since the duration of pre-T1 206, and midst-T2 208 are dependent on the speed in which the floor cleaning machine 204 is moving, the ratiometric mixing of water 102 and the ozonated concentrate liquid 118 can be dynamically altered based on the speed of the floor cleaning machine 204. In this regard, the aqueous ozone floor disinfection system 100 can be configured to monitor the speed of the floor cleaning machine and with speed increases, that can cause a shortening of ozone disinfection spray contact time from nozzle 112 in the pre-hygienic zone 204A pre-T1 206, and nozzle 114 in the midst-hygienic zone 204B midst-T2 208, increase the predetermined pre-hygienic ozone treatment concentration and the predetermined midst-hygienic ozone treatment concentration accordingly. The converse can also be true, speed decreases of the floor cleaning machine can increase the ozone disinfection spray contact time from nozzle 112 in the pre-hygienic zone 204A pre-T1 206, and nozzle 114 in the midst-hygienic zone 204B midst-T2 208 thus the predetermined pre-hygienic ozone treatment concentration and the predetermined midst-hygienic ozone treatment concentration can be decreased accordingly.

In the present invention the term "ratiometric" or "ratiometrically" is intended to mean a system in which an output is directly proportional to an input. In this regard, the output in an ozonated water mixture is a ratio of an ozonated concentrate liquid and water. An advantage, in the present invention, is the ozonated concentrate liquid can have a higher ozone concentration than needed and ratiometrically can be diluted down with water to make the ozone concentration that is needed. Additionally, the ozonated concentrate liquid can be ratiometrically mixed through different mixers with water to produce different ozone water having different ozone concentrations that can be used in exemplary embodiments of the present invention. Another advantage and in lieu of batch type techniques, no matter what the volume of outflow solution is needed ratiometrically mixing the water and ozonated concentrate liquid can produce the needed volume at the right ozone concentration accurately at any on-demand volume level.

Figure 5:
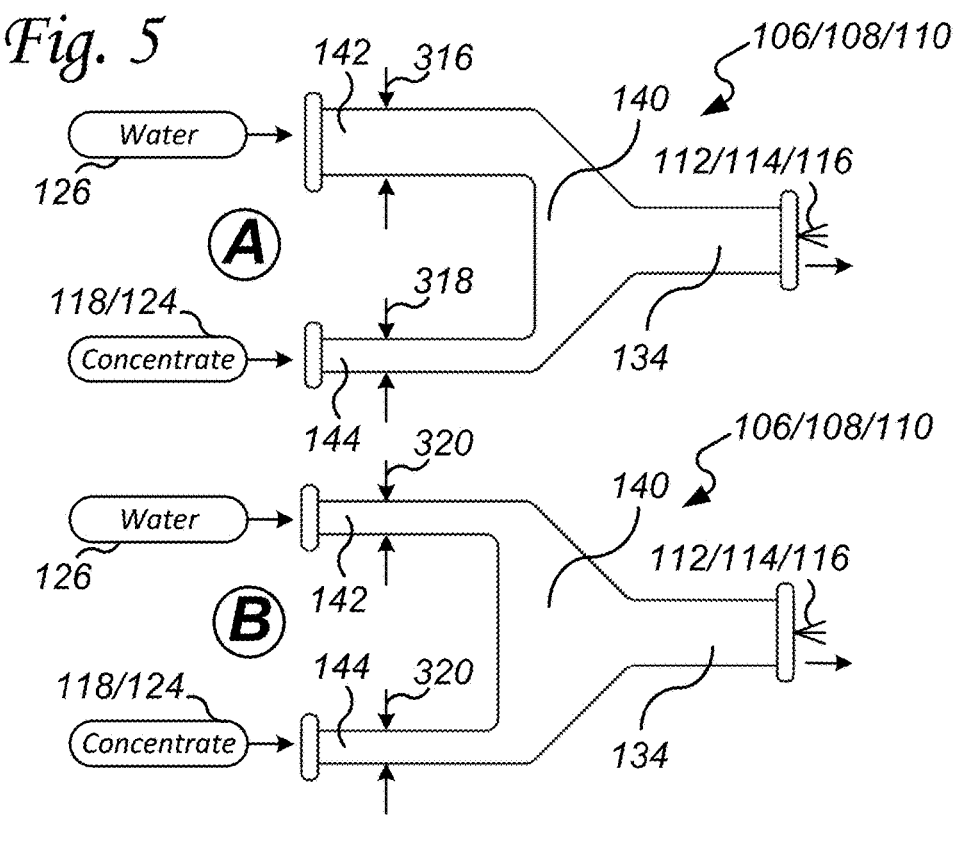
FIG. 5 illustrates examples of a ratiometric mixer.

In operation, with reference to at least FIG. 5 reference 'A', mixing can be done with a fixed orifice type manifold 140 where each orifice 316/318 is a different diameter creating the desired ratio of water 126 and ozonated concentrate liquid 124 creating a single outflow 134 to spray nozzles 112/114/116.

In an exemplary embodiment, each of the pre-hygienic mixer 106, midst-hygienic mixer 108, and post-hygienic mixer 110 can comprise a water inlet 142 for receiving the water source 102, a concentrate inlet 144 for receiving the ozonated concentrate liquid 118/124, and a single mixed outflow 134. The flow volume through the water inlet 142 and the concentrate inlet 144 are sized 316/318 to passively mix the pre-hygienic ozone disinfection solution at the predetermined pre-hygienic ozone treatment concentration, the midst-hygienic ozone disinfection solution at the predetermined midst-hygienic ozone treatment concentration, and the post-hygienic ozone disinfection solution at the predetermined post-hygienic ozone treatment concentration. For disclosure and clarification, in a plurality of exemplary embodiments, at least one of the pre-hygienic mixer 106, midst-hygienic mixer 108, or post-hygienic mixer 110 can be incorporated into the system, perhaps not all three in every embodiment.

Figure 7:
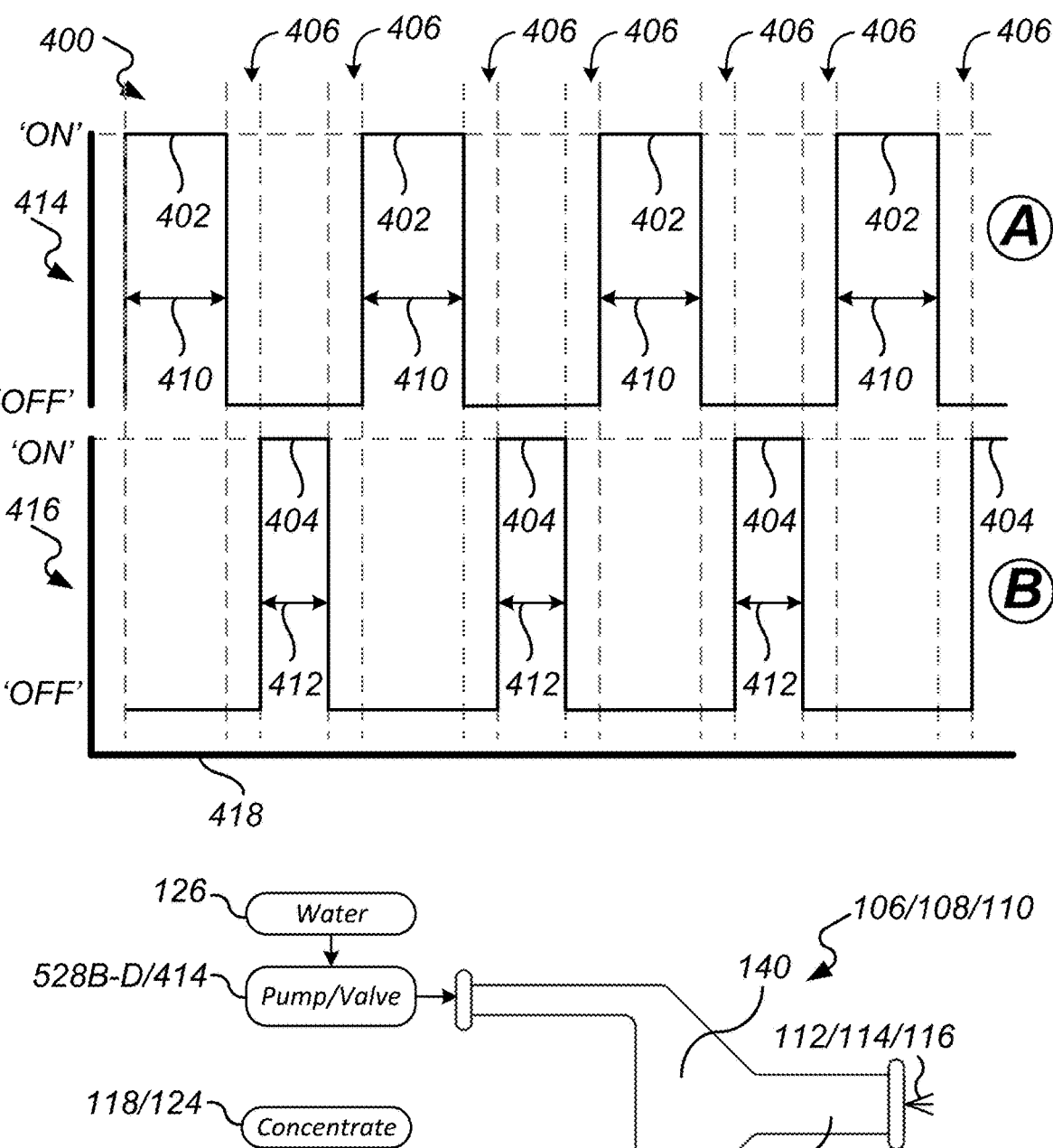
FIG. 7 illustrates one example of mixing pulse sequence by way of transitioning between pump/valve activation pulses.

Alternatively, with reference to at least FIGS. 5 and 7, a fixed orifice type manifold 140 can have the same size orifices 320, and pumps/valves 528/532 can be used to dispense water 126 and ozonated concentrate liquid 124 under control 414/416 to create the desired ratio of water and ozonated concentrate liquid to spray 112/114/116. An advantage of using pumps 528/532 and control system 500 timing 414/416 is that the concentration of the ozone water mixture can be dynamically changed. In this regard, as the floor cleaning machine 202 speeds up or slows down, and for other reasons and situations, the concentration of the ozone water mixtures through nozzles 106/108/110 can be changed by adjusting the pulse width timing 414/416 that operates the pumps 528/532. Including stopping the pulse width generation to stop mixing and spraying the ozone water mixtures through nozzles 106/108/110.

An advantage, in the present invention, is that the aqueous ozone generator 530 produces ozone through water electrolysis and ion exchange techniques. In this regard, part of the aqueous ozone generator 530 can comprise an electrochemical generator 516. During normal operation, the process of generating aqueous ozone can degrade the aqueous ozone generator 530. In addition, water quality can have an impact on the aqueous ozone generator 530 including causing premature scaling of certain components. This creates the need to track the service life of the aqueous ozone generator 530 and components such as the electrochemical generator 516. The present invention does this in a couple of different ways.

In an exemplary embodiment, in one example, technician 302 can test the ozonated water manually data communicating the results by way of computing device 732 such as a laptop, smartphone, tablet, or other suitable computing device for recording on a remote data processing resource 702 such as a server 702. Ozone production, use of the aqueous ozone generator, and ozone concentration levels can then be tracked remotely over time. When data shows that service or replacement is needed notification can be sent to technician 302 or administrators 304 and the aqueous ozone generator 530 serviced or replaced.

In another exemplary embodiment, the control system 500 can comprise an ozone sensor 522 and communication interface 508 that can automatically monitor ozone production and use of the aqueous ozone generator 530. The results can be data communicated by way of the communication interface 508 to remote data processing resources 702 for recording. When data shows that service or replacement is needed notification can be sent to technician 304 or administrators 304 and the aqueous ozone generator 530 services or replaced.

Figure 11:
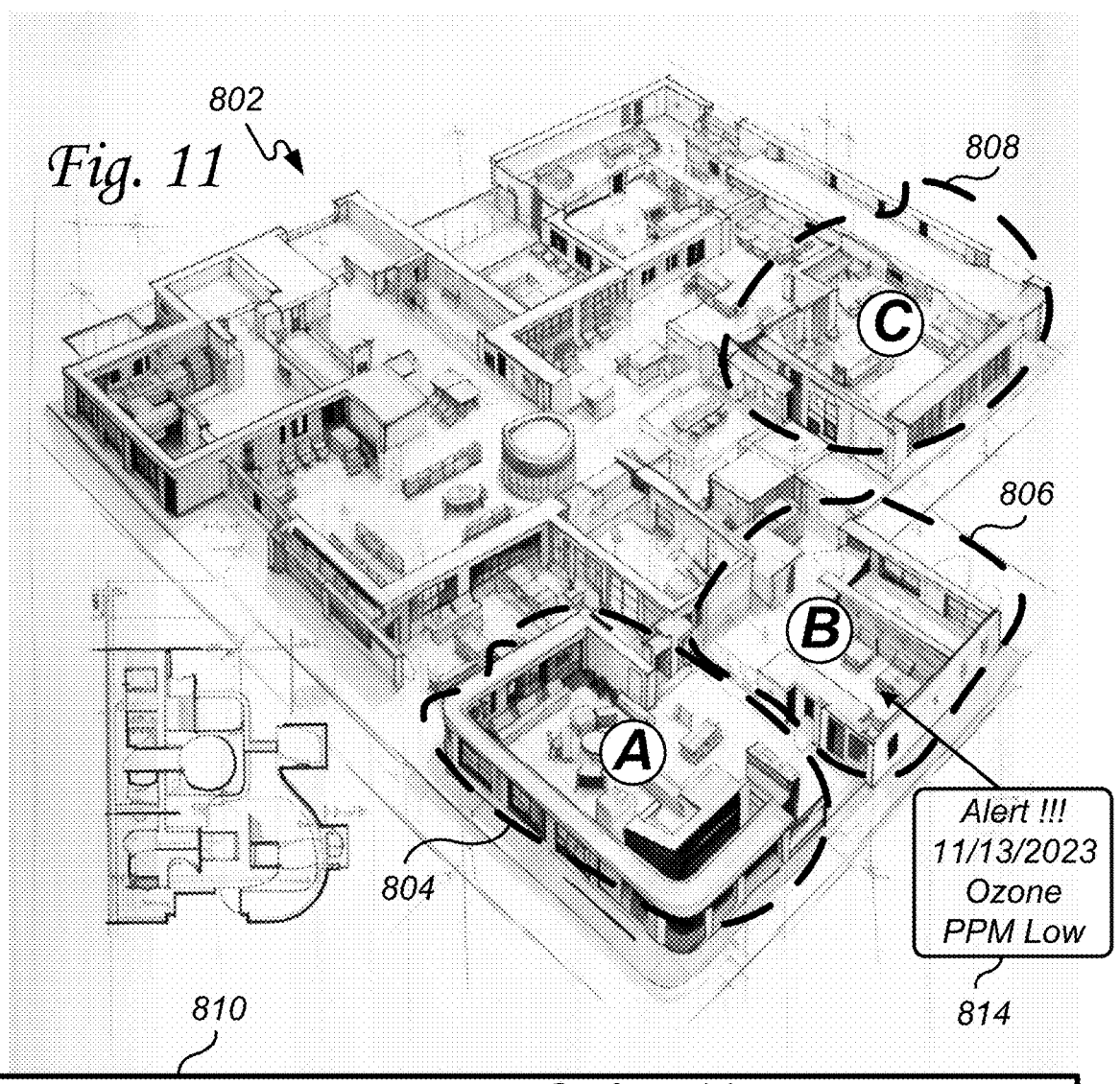
FIG. 11 illustrates one example of a floor plan to monitor geofenced floor surfaces that have been treated with the post-hygienic ozone disinfection solution.

Another advantage, in the present invention, and with reference to at least FIG. 11, is that the control system 500 can comprise a global positioning system (GPS) 514. In this regard, the GPS location of the floor cleaning machine 202 during use and more specifically the areas that have been treated by the aqueous ozone floor disinfection system can be monitored, tracked, and data communicated by way of the communication interface to the remote data processing resource 702. Reports, maps, and other information can then be used to inform where, when, and other details of floor surface 204 ozone disinfection, and may be required and/or desired in a particular embodiment.

With reference to FIG. 1, reference 'A' illustrates a system diagram of the aqueous ozone floor disinfection system.

During operation, water 102 is routed to an aqueous ozone generator 530. Through electrolysis and ion exchange techniques the aqueous ozone generator 530 produces an ozonated concentrate liquid 118. The concentration of the ozonated concentrate liquid 118 can be significantly higher than what will be dispensed on the floor surface 204. In this regard, the ozonated concentrate liquid 118 can be routed 120 to mixers 106/108/110. Additionally, water 102 can be routed 104 to mixers 106/108/110. Such routing 104/120 as well as other types and kinds of routing can be by way of tubing or other suitable fluid communication means, as may be required and/or desired in a particular embodiment.

Each of the mixers 106/108/110 ratiometrically and mutually exclusively mixes the water 102 and the ozonated concentrate liquid 118 into an ozone treatment concentration solution which is then sprayed in different zones 204A/204B/204C on the floor surface 204. In this regard, pre-hygienic ratiometric mixer 106 mixes a pre-hygienic ozone disinfection solution having a predetermined pre-hygienic ozone treatment concentration that can be sprayed by way of nozzle 112 within the pre-hygienic zone 204A. Correspondingly, the midst-hygienic ratiometric mixer 108 mixes a midst-hygienic ozone disinfection solution having a predetermined midst-hygienic ozone treatment concentration that can be sprayed by way of the nozzle 114 within the midst-hygienic zone 204B. Correspondingly, post-hygienic ratiometric mixer 110 mixes a post-hygienic ozone disinfection solution having a predetermined post-hygienic ozone treatment concentration that can be sprayed by way of nozzle 116 within the post-hygienic zone 204C.

An advantage, in the present invention, is that a different concentration of dissolved ozone can be ratiometrically mixed and dispensed from each of nozzles 112/114/116. In this regard, the predetermined pre-hygienic ozone treatment concentration can be different from the predetermined midst-hygienic ozone treatment concentration which can be different from the predetermined post-hygienic ozone treatment concentration. In operation, the dissolved ozone concentration can be applied to the floor surface 204 in different concentrations since the floor surface 204 is in different states in the pre-hygienic zone 204A (uncleaned with debris), midst-hygienic zone 204B (during cleaning with agitation, water, detergent, and debris), and post-hygienic zone 204C (clean) areas requiring different types of treatment concentration levels.

Additionally, if a high ozone concentration level is desired and it is desired to isolate the higher level of ozone concentration, from contact with technician 302 or to minimize ozone odor during cleaning, the higher level of ozone concentration treatment can be applied in the midst-hygienic 204B zone when it is sprayed as part of washing and then removed with the water, detergent, and debris from the floor surface.

Referring to FIG. 1 references 'B' and 'C' illustrate examples of floor cleaning machines 202 that use brushes, detergents sprayed on floor surfaces, vacuum, and other elements to wash and remove dirty waste liquid from floor surfaces. In general, the present invention can be integrated into new or retrofitted to old floor cleaning machines 202 that are absent adequate floor surface disinfection capabilities.

An advantage, in the present invention, is that when considering the floor cleaning machine 202 moving 212 along a floor surface 202 three regions are defined. In this regard, a pre-hygienic zone 204A or pre-cleaned region transitions 216 to a midst-hygienic zone 204 or a region currently being cleaned by the floor cleaning machine 204 cleaning mechanism, that transition 214 to a post-hygienic zone 204C or cleaned floor surface. While there are embodiments of the present invention that seek to treat two or more regions (pre-hygienic 204A, midst-hygienic zone 204B, and/or post-hygienic 204C) with varying ozone concentration levels, the present invention can also reach a high level of floor surface disinfection even reaching sterile or near sterile levels of floor surface 204 disinfection conditions with only the use of the post-hygienic mixer 110 and nozzle 116 spraying a post-hygienic ozone disinfection solution having a predetermined post-hygienic ozone treatment concentration within the post-hygienic zone 204C. In this regard, floor surface 204 sterile or near sterile conditions can occur when the post-hygienic ozone disinfection solution is sprayed at a sufficient ozone concentration level, within the post-hygienic zone 204C, immediately after the floor surface 204, in the midst-hygienic zone 204B, is cleaned of debris, where the post-hygienic ozone disinfection solution can remain undisturbed, unagitated, and undiluted by cleaning liquids for a longer treatment time post-T3 210 to air dry.

In an exemplary embodiment, an aqueous ozone floor disinfection system 100 can comprise an aqueous ozone generator 530 that receives a portion of a water source 102 and generates from the water source 102 an ozonated concentrate liquid 118. Such aqueous ozone production can be by way of an electrochemical generator 516. The electrochemical generator 516 can be integrated into the aqueous ozone generator 530. Additionally, the electrochemical generator 516 can comprise an ion exchange material 534 that facilitates ozone molecule formation/production. In operation, the aqueous ozone generator 530 can use electrolysis in combination with the ion exchange material 534, other coatings, electronic control signals, pulse width modulation, and/or other techniques, technologies, and signal processing to produce an ozonated concentrate liquid in the range of 1 part per million ozone (ppm) or other desired lower limit to 10 ppm or other desired upper limit depending on several factors. Such factors can include the aqueous ozone generator 530, electrochemical generator 516 construction, the quantity of ozonated concentrate liquid 518 produced at a time, the amount of time allowed for the aqueous ozone generator 530 to produce the ozonated concentrate liquid 518, the amount of electrical current passed between electrodes and the surface area of the electrodes, and other factors.

While the type and kind of components in the aqueous ozone generator 530 and in particular the electrochemical generator 516 are selected to promote a maximum service life of the electrochemical generator 516, the process of making ozonated concentrate liquid 118 can consume certain of the materials in the aqueous ozone generator 530 and/or the electrochemical generator 516 thus there is a useful service life of the aqueous ozone generator 530 that needs to be monitored.

In addition, during normal use of the aqueous ozone generator 520 and/or electrochemical generator 517, the type or kind of water used in the generator can influence aqueous ozone production (quantity and production rate) as well as create undesirable scaling of the electrodes which to can adversely impact the production of ozonated concentrate liquid 118.

In an exemplary embodiment, the control system 500 by way of an electrical current sensor 520 can monitor and adjust the electrical current pass between electrodes. In this regard, adjustments to the amount of electrical current supplied to the aqueous ozone generated to overcome minor degradation of consumable electrodes, and other factors that would normally and through the water during aqueous ozone production.

While adjusting the electrical current aids in the generation of consistent and reliable aqueous ozone production at desired ppm concentrations, the control system 500 can determine how much it has to compensate over a nominal state, such as when the aqueous ozone generator 530 was newly installed. Such electrical current monitoring and adjustment details can be reported or otherwise data communicated, by way of communication interface 508, to a remote data processing resource 702 such as a server 702. Such monitoring and tracking of electrical current use and changes over time plus other factors can be used to predict the service life of the aqueous ozone generator 530 and provide notifications to technicians 302 or administrators 304 when it is time to schedule maintenance and/or replacement of the aqueous ozone generator 530.

In addition to predictive maintenance and service life notifications of the aqueous ozone production components, changes in water 102 quality, or detection of water mineral scale buildup on the aqueous ozone generator 530 components can be detected and technicians 302 or administrators 304 can be notified to take the necessary corrective action.

In an exemplary embodiment, during operation, when ozone disinfection of the post-hygienic zone 204C is desired, the post-hygienic mixer 116 receives and ratiometrically blends a portion of the ozonated concentrate liquid 118 and a portion of the water source 102 to form a post-hygienic ozone disinfection solution having a predetermined post-hygienic ozone treatment concentration (based on the ratio of water 102 and ozonated concentrate liquid 118 mix) which will be less than ozone concentration of the ozonated concentrate liquid 118. In this regard, the concentrated liquid 118 mix is diluted down by the water to the desired ozone concentration level (ppm).

In operation, the predetermined post-hygienic ozone treatment concentration is selected to achieve sterilization or near sterilization of the floor surface 204 within a post-hygienic treatment time post-T3 210. In this regard, the post-hygienic treatment time is greater than the cleaning period midst-T2 208. A post-hygienic nozzle 116 is mounted on the floor cleaning machine 202 proximate the transition 214 between the midst-hygienic zone 204B and the post-hygienic zone 204C. The post-hygienic nozzle 116 directs the spray of the post-hygienic ozone disinfection solution onto the post-hygienic zone portion 204C of the floor surface 204.

In operation, cleaning within the midst-hygienic zone 204B removes debris from the floor surface 204 allowing the post-hygienic ozone disinfection solution sprayed 116 on the post-hygienic zone 204C to contact the floor surface in an unencumbered by debris manner for at least the post-hygienic treatment time absent agitation or removal by the floor cleaning machine 202 improving disinfection of the floor surface.

In an exemplary embodiment, during operation, when ozone disinfection of the midst-hygienic zone 204B is desired the midst-hygienic mixer 108 receives and ratiometrically blends a portion of the ozonated concentrate liquid 118 and a portion of the water source 102 to form a midst-hygienic ozone disinfection solution having a predetermined midst-hygienic ozone treatment concentration. The predetermined midst-hygienic ozone treatment concentration is selected to achieve disinfection of debris on the floor surface within a midst-hygienic treatment time midst-T2 208. The midst-hygienic treatment time is equal to the cleaning period midst-T2 208. In operation, a midst-hygienic nozzle 114 is mounted on the floor cleaning machine 202 proximate to the midst-hygienic zone 204B. The midst-hygienic nozzle 114 directs spray of the midst-hygienic ozone disinfection solution onto the midst-hygienic zone 204B portion of the floor surface 204.

In an exemplary embodiment, during operation, when ozone disinfection of the pre-hygienic zone 204A is desired the pre-hygienic mixer 106 receives and ratiometrically blends a portion of the ozonated concentrate liquid 118 and a portion of the water source 102 to form a pre-hygienic ozone disinfection solution having a predetermined pre-hygienic ozone treatment concentration. The predetermined pre-hygienic ozone treatment concentration is selected to achieve disinfection of debris on the floor surface 204 within a pre-hygienic treatment time pre-T1 206. The pre-hygienic treatment time pre-T1 206 is less than the cleaning period midst-T2 208. A pre-hygienic nozzle 112 is mounted on the floor cleaning machine 202 proximate the transition 216 between the midst-hygienic zone 204B and the pre-hygienic zone 204A. The pre-hygienic nozzle 112 directs the spray of the pre-hygienic ozone disinfection solution onto the pre-hygienic zone 204A portion of the floor surface 204.

In an exemplary embodiment, the aqueous ozone floor disinfection system 100 can comprise a cleaning mechanism 220 that is capable of traversing a floor surface 204 and cleaning the floor surface 204. An aqueous ozone generator 530 receives water 102 and generates an ozonated concentrate liquid 118 from the water 102. A mixer 110 receives and ratiometrically blends a portion of the ozonated concentrate liquid 118 with water 102 to form an ozone disinfection solution 118 at a desired ozone concentration level. A nozzle 116 sprays the ozone disinfection solution 118 onto the floor surface 204C after it has been cleaned by the cleaning mechanism 220.

In an exemplary embodiment, a method of using an aqueous ozone floor disinfection system can comprise the steps of operating a cleaning mechanism 220 on a floor surface 204 and creating an ozonated concentrate liquid 118 from water 102 with an aqueous ozone generator 530.

The method continues by creating an ozone disinfection solution at a desired concentration level with a mixer 110 that receives and ratiometrically blends a portion of the ozonated concentrate liquid 118 with water 102, and disinfecting the floor surface by spraying the ozone disinfection solution onto the floor surface with a nozzle 116 after it has been cleaned by the cleaning mechanism 220.

Figures 2, 3:
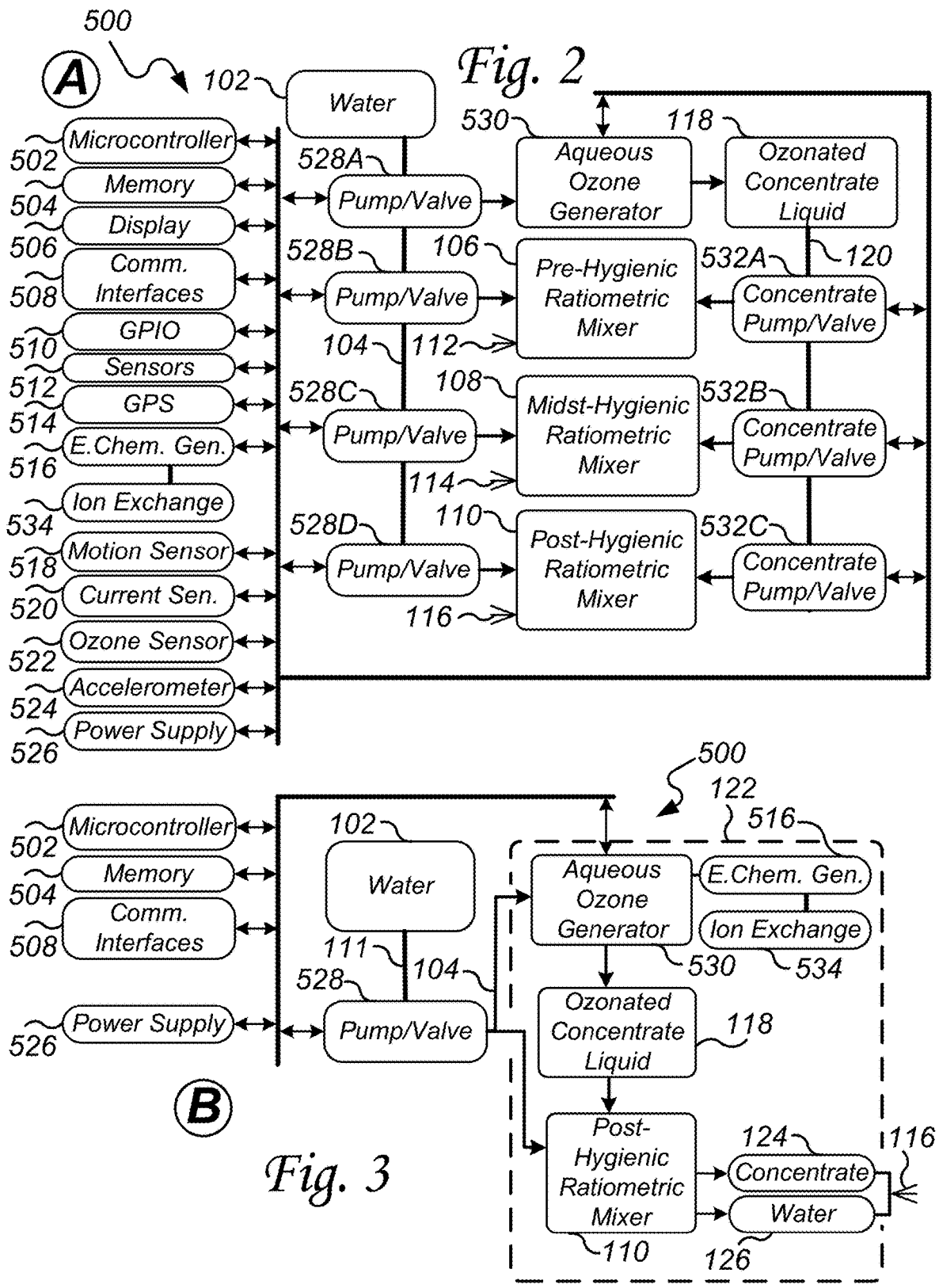
FIGS. 2-3 illustrate examples of a control system for an aqueous ozone floor disinfection system.

Referring to FIG. 2, there is illustrated one example of a control system 500 for an aqueous ozone floor disinfection system 100. In an exemplary embodiment, control system 500 can be integrated into and be responsive to the action of a floor cleaning machine 202. In addition, control system 500 can be a web-enabled control system.

The term "web-enabled" or "web-enabled control system" or "web-enabled control system 500" in the present invention is intended to mean an Internet-of-things device. In this regard, a device that is capable of connecting a physical device such as an aqueous ozone disinfection system or a floor cleaning machine 202 to the digital world. Stated differently, web-enabling is equipping a device with the necessary electronics to be monitored, and controlled, and data communicate locally and remotely with other data-communicating devices. Such other data-communicating devices can be smartphones, tablets, laptops, mobile communication devices, other web-enabled devices, remote data processing resources, servers, and similar devices.

Figure 8:
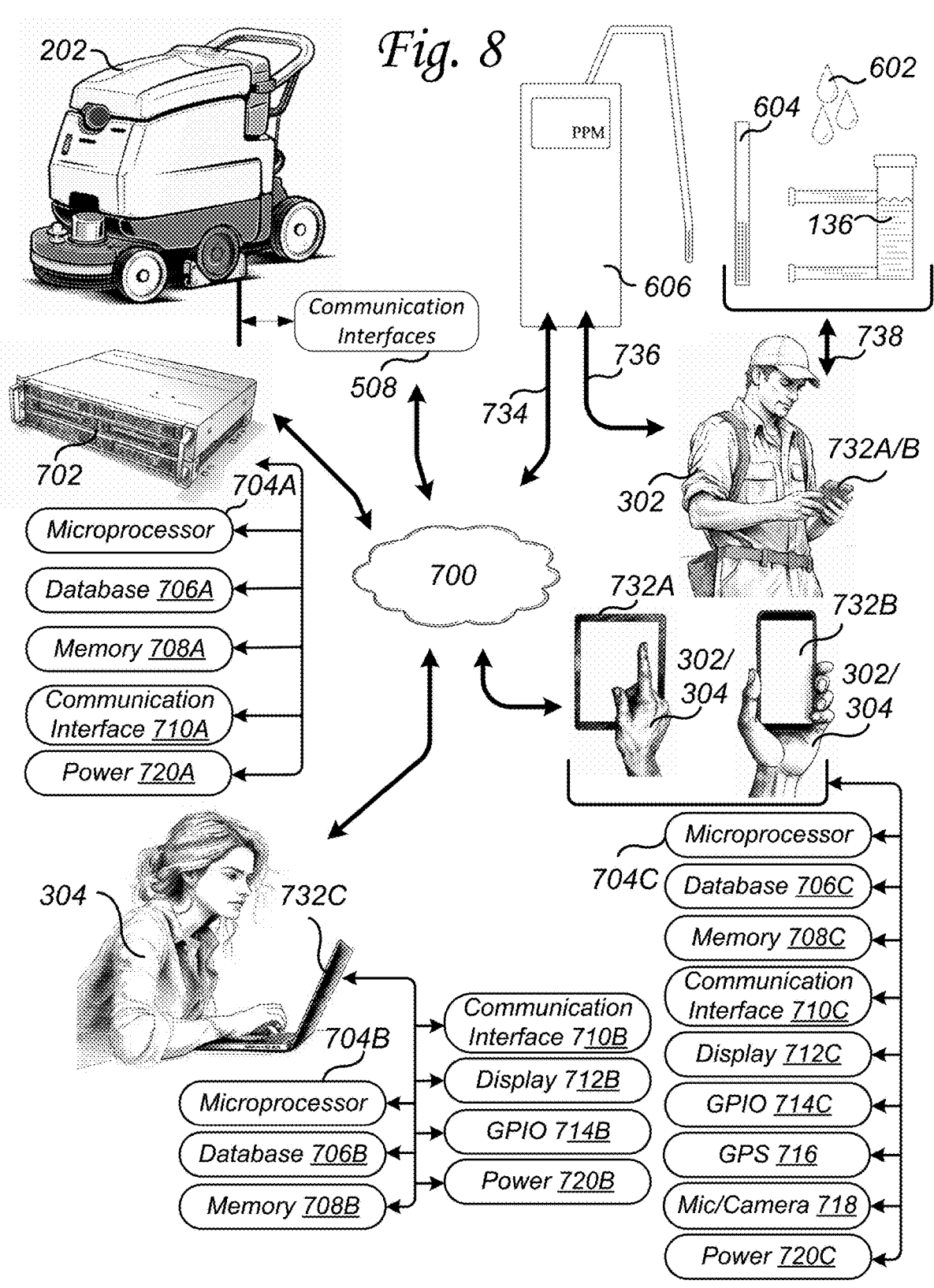
FIG. 8 illustrates one example of a system and network diagram.

In addition, and with reference to at least FIG. 8, such data communicating devices 732 can data communicate with remote data processing resources 702 and store and retrieve data from databases 706A-C, and other data processing resources, as may be required and/or desired in a particular embodiment. Laptops, smartphones, smartwatches, tablets, desktop computers, servers, mobile communication devices, and other types and kinds of data communication devices can all be data communicating devices 732 also referred to as computing devices 732.

In operation, a technician 302, an administrator 304, or other authorized people can use computing device 732 to interact with the aqueous ozone generator 100 or floor cleaning machine 202. In this regard, a technician 302 can be a person who operates, maintains, cleans, configures, repairs and performs other functions on or with the aqueous ozone generator 100 or floor cleaning machine 202. An administrator 304 can be a person who administers, provides remote service or technical support, or be other types or kinds of authorized user, as may be required and/or desired in a particular embodiment.

In an exemplary embodiment, technician 302 can record 736/738 ozone test results and receive data related to the aqueous ozone floor disinfection system 100. Such test results can be taken or otherwise generated with ozone concentration test implements 602/604/606 which can include an ozone concentration test strip 604, an ozone concentration test drops 602, or an ozone concentration test device 606 to test for dissolved ozone, or other types and/or kinds of ozone concentration test implement. Technician 302 can manually enter the test results in a computing device 732A/B. As better illustrated in at least FIG. 10, a software application or website can be used in combination with the computing device 732A/B to identify the aqueous ozone floor disinfection system 100, record the test results, and see other useful data by way of data communicating with a remote data processing resource 702. In some embodiments, certain ozone concentration test devices 606 may have the ability to data communicate 734 directly with a remote data processing resource 702, eliminating the need for computing device 732A/B to act as an intermediary device to record test results on the remote data processing resource 702.

Such data processing resources can be a server or other types and kinds of data processing resources. Furthermore, data communicating devices 732, remote data processing resources 702, data storage resources 706A-C, and other types and kinds of data communicating devices can data communicate over a global network 700. The Internet is a global network 700.

In an exemplary embodiment and with reference to at least FIG. 2, the aqueous ozone generator 100 can be equipped with a web-enabled control system 500. Such a web-enabled control system 500 can comprise a microcontroller 502 which is operationally related to a memory 504, a display 506, a plurality of communication interfaces 508, general purpose input and outputs (GPIO), a plurality of sensors 512, a global position system (GPS) 514, an electrochemical generator 516, a plurality of motion sensors 518, a plurality of electrical current sensors 520, a plurality of ozone sensors 522, an accelerometer 524, a power supply 526, a plurality of pumps/valves 528/532, and an aqueous ozone generator 530.

The microcontroller 502 can be INTEL, ZILOG, MICRO-CHIP, AMD, ARM, and/or other types or kinds of microcontrollers.

The memory 504 can be a combination of RAM, ROM, flash, hard drives, solid-state drives, USB flash drives, and/or other types and kinds of memory.

The display 506 can be an LCD, OLED, LED, as well as have touch input capabilities and/or other types and kinds of displays and user inputs as may be required and/or desired in a particular embodiment.

The communication interface 508 can be LAN, WAN, USB, Ethernet, RS232, RS485, serial, WiFi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

In an exemplary embodiment, the communication interface 508 is operationally related to the microcontroller 502. The control system by way of the communication interface 508 data communicates with the remote data processing resource 702, data communication devices 732, and other data processing resources in a local area network environment or a wide area network environment across a global network 700 in a wired or wireless manner as may be required and/or desired in a particular embodiment. The Internet is a global network 700.

The GPIO 510 can be TTL, CMOS, transistors, buffers, relays, pushbuttons, switches, and/or other types and kinds of GPIO circuits.

The sensors 512 and/motion sensor 518 can be passive infrared (PIR) motion sensors, infrared, thermal, Doppler radar, ultrasonic, capacitance, touch-type, optical, Hall effect, switch, fingerprint, and other types of biometric sensors, and/or other types and kinds of sensors. Additionally, sensor 512 can be ambient condition sensors such as temperature, moisture, humidity, sunlight, and/or other types and kinds of sensors.

In an exemplary embodiment, analog-type sensor determinations can be converted to digital values so that the microcontroller 502 can process the data. Alternatively, the microcontroller 502 can perform analog-to-digital conversions if equipped to perform such functions.

The electrochemical generator 516 can be an electrolysis-based device that utilizes ion exchange material 534 and other devices and processes to produce chemical compounds from water such as ozone $O_3$.

The current sensor 520 can be configured to measure the supply electrical current to the electrochemical generator 516, the aqueous ozone generator 530, a combination 516/530 thereof, and/or other devices and systems, as may be required and/or desired in a particular embodiment.

The ozone sensor 522 can be configured to monitor the ozone concentration of one or more of the ozonated concentrate liquid 118, the post-hygienic ozone disinfection solution, the midst-hygienic ozone disinfection solution, the pre-hygienic ozone disinfection solution, or other sources of ozonated liquid, as may be required and/or desired in a particular embodiment.

The accelerometer 524 can be configured to monitor the motion of the floor cleaning machine 202, or other systems and devices associated with the floor cleaning machine 202.

The power supply 526 can be AC, DC, battery, solar, and/or other types and kinds of power supplies.

The pumps and/or valves 528A-D/532A-C, in addition to performing their fluid handling tasks, can be actuated and/or controlled by way of a relay, MOSFET, or other types and kinds of controlling devices. In addition, other pumps and/or valves 528/532 can be integrated into the system as may be required and/or desired in a particular embodiment.

The aqueous ozone generator 530 receives water as an input and uses the electrochemical generator 516 which is integrated into the aqueous ozone generator 530 to produce high concentrations of aqueous ozone molecules. Such concentrations of aqueous ozone can range from 1 ppm to 10 ppm or other desired range, as may be required and/or desired in a particular embodiment.

In an exemplary embodiment, a user interface for the aqueous ozone disinfection system 100 comprises at least one of the following a display 506, a display 506 with touchscreen, a communication interface 508 configured to data communicate with a remote data processing resource 702 such as a server 702 and/or a computing device 732.

The user interface for the aqueous ozone disinfection system 100 can further comprise a plurality of button input capabilities by way of the GPIO 510, or other user interfaces. The user interface is operationally related to the microcontroller 502.

In an exemplary embodiment, a post-hygienic pump 528D/532C can be configured to control the egress of the post-hygienic ozone disinfection solution from the post-hygienic nozzle 116. The post-hygienic pump 528D/532C can be configured to push water 102 and ozonated concentrate liquid 118 through the post-hygienic mixer 110 under pressure and out of the post-hygienic nozzle 116 as illustrated in at least FIG. 2, or the post-hygienic pump can be configured on the output side of the post-hygienic mixer 110 and pull the water 102 and ozonated concentrate liquid 118 through the post-hygienic mixer 110 and push it out the post-hygienic nozzle 116. Additionally, the post-hygienic pump 528D/532C can be configured as more than one pump that moves more than one liquid source (water and ozonated concentrate liquid), or configured as a single pump that receives the ratiometrically mixed post-hygienic ozone disinfection solution, or configured in other ways, as may be required and/or desired in a particular embodiment.

In operation, the control system 500 can comprise a microcontroller 502, a memory 504, the post-hygienic pump 528D/532C, and a motion sensor 518. The microcontroller 502 is operationally related to the memory 504, the post-hygienic pump 528D/532C, and the motion sensor 518. The memory 504 is encoded with instructions that when executed by the microcontroller 502 perform the step of dispensing the post-hygienic ozone disinfection solution by way of the post-hygienic pump 528D/532C when the motion sensor 518 detects the floor cleaning machine 202 is moving in manner that is creating the post-hygienic zone 204C.

In a second exemplary embodiment, a midst-hygienic pump 528C/532B can be configured to control the egress of the midst-hygienic ozone disinfection solution from the midst-hygienic nozzle 114. The midst-hygienic pump 528C/532B can be configured to push water 102 and ozonated concentrate liquid 118 through the midst-hygienic mixer 108 under pressure and out of the midst-hygienic nozzle 114 as illustrated in at least FIG. 2, or the midst-hygienic pump can be configured on the output side of the midst-hygienic mixer 108 and pull the water 102 and ozonated concentrate liquid 118 through the midst-hygienic mixer 108 and push it out the midst-hygienic nozzle 114. Additionally, the midst-hygienic pump 528C/532B can be configured as more than one pump that moves more than one liquid source (water and ozonated concentrate liquid), or configured as a single pump that receives the ratiometrically mixed midst-hygienic ozone disinfection solution, or configured in other ways, as may be required and/or desired in a particular embodiment.

In operation, the control system 500 can comprise a microcontroller 502, a memory 504, the midst-hygienic pump 528C/532B, and a motion sensor 518. The microcontroller 502 is operationally related to the memory 504, the midst-hygienic pump 528C/532B, and the motion sensor 518. The memory 504 is encoded with instructions that when executed by the microcontroller 502 perform the step of dispensing the midst-hygienic ozone disinfection solution by way of the midst-hygienic pump 528C/532B when the motion sensor 518 detects the floor cleaning machine 202 is moving in a manner that is creating the post-hygienic zone 204C.

In a third exemplary embodiment, a pre-hygienic pump 528B/532A can be configured to control the egress of the pre-hygienic ozone disinfection solution from the pre-hygienic nozzle 112. The pre-hygienic pump 528B/532A can be configured to push water 102 and ozonated concentrate liquid 118 through the pre-hygienic mixer 106 under pressure and out of the pre-hygienic nozzle 112 as illustrated in at least FIG. 2, or the pre-hygienic pump can be configured on the output side of the pre-hygienic mixer 106 and pull the water 102 and ozonated concentrate liquid 118 through the pre-hygienic mixer 106 and push it out the pre-hygienic nozzle 112. Additionally, the pre-hygienic pump 528B/532A can be configured as more than one pump that moves more than one liquid source (water and ozonated concentrate liquid), or configured as a single pump that receives the ratiometrically mixed pre-hygienic ozone disinfection solution, or configured in other ways, as may be required and/or desired in a particular embodiment.

In operation, the control system 500 can comprise a microcontroller 502, a memory 504, the pre-hygienic pump 528C/532B, and a motion sensor 518. The microcontroller 502 is operationally related to the memory 504, the pre-hygienic pump 528C/532B, and the motion sensor 518. The memory 504 is encoded with instructions that when executed by the microcontroller 502 perform the step of dispensing the pre-hygienic ozone disinfection solution by way of the pre-hygienic pump 528B/532A when the motion sensor 518 detects the floor cleaning machine 202 is moving in a manner that is creating the post-hygienic zone 204C.

In another exemplary embodiment, the memory 504 can be encoded with instructions that when executed by the microcontroller 502 perform the step of preventing the floor cleaning machine 202 from operating if the aqueous ozone generator is not operating correctly. In this regard, if the ozonated concentrate liquid 118 is not being produced for some reason, control system 500 can prevent the floor cleaning machine 202 from operating, so that a situation where technician 302 thinks the floor surface is being disinfected but in reality, it is not. Once the aqueous ozone generation is restored the floor cleaning machine 202 can be placed back in service by control system 500.

Referring to FIG. 3 in reference 'A', there is illustrated one example of a control system 500 for an aqueous ozone floor disinfection system 100. In an exemplary embodiment in reference 'B', many of the components of the aqueous ozone floor disinfection system 100 can be integrated together 122 or packaged together to reduce the size, cost, and complexity of the system. In this regard, in an application where only a single post-hygienic zone treatment and nozzle 116 are used components like the aqueous ozone generator 530, electrochemical generator 516, ozonated concentrate liquid 118 product and storage and post-hygienic mixer 110 can be integrated or otherwise package together 122.

An advantage, in the present invention, is that the post-hygienic mixer 110 can ratio the flow of the water 102 and the ozonated concentrate liquid 118 but not mix them.

Rather, a ratio amount of the concentrate stream 126 and a ratio amount of the water stream 126 can be fed into the post-hygienic nozzle 116 and sprayed in a manner that ozonated concentrate 124 and water 126 mix at the point of departure from the post-hygienic nozzle 116 or in the air as they are sprayed. If desired the pre-hygienic and/or the midst-hygienic portion of the aqueous ozone floor disinfection system 100 can be configured in a similar manner, as may be required and/or desired in a particular embodiment.

In an exemplary embodiment, an aqueous ozone floor disinfection system 100 that is used on the post-hygienic zone 204C treatment and nozzle 116, can comprise a water source 102, and a floor cleaning machine 202. The floor cleaning machine 202 can comprise a cleaning mechanism 220. The floor cleaning machine 202 is capable of traversing a floor surface 204 entering a pre-hygienic zone 204A prior to cleaning, cleaning within a midst-hygienic zone 204B for a cleaning period midst-T2 208 by way of the cleaning mechanism 220, and moving away from the midst-hygienic zone 204B creating a post-hygienic zone 204C.

The aqueous ozone floor disinfection system 100 further comprises an aqueous ozone generator 530 that receives a portion of the water source 102 and generates from the water source 102 an ozonated concentrate liquid 118.

The aqueous ozone floor disinfection system 100 further comprises a post-hygienic mixer 110 that receives and ratiometrically blends a portion of the ozonated concentrate liquid 118 and a portion of the water source 102 to form a post-hygienic ozone disinfection solution having a predetermined post-hygienic ozone treatment concentration which is less than ozone concentration of the ozonated concentrate liquid 118. The predetermined post-hygienic ozone treatment concentration is selected to achieve sterilization of the floor surface 204 within a post-hygienic treatment time post-T3 210. The post-hygienic treatment time post-T3 210 is greater than the cleaning period midst-T2 208.

The aqueous ozone floor disinfection system 100 further comprises a post-hygienic nozzle 116 that is mounted on the floor cleaning machine 202 proximate to the transition 214 between the midst-hygienic zone 204B and the post-hygienic zone 204C. The post-hygienic nozzle 116 directs the spray of the post-hygienic ozone disinfection solution onto the post-hygienic zone portion 204C of the floor surface 204.

In operation, cleaning within the midst-hygienic zone 204B removes debris from the floor surface 204 allowing the post-hygienic ozone disinfection solution sprayed on the post-hygienic zone 204C to contact the floor surface 204 in an unencumbered by debris manner for at least the post-hygienic treatment time post-T3 210 absent agitation or removal by the floor cleaning machine 202 improving disinfection of the floor surface.

Figure 4:
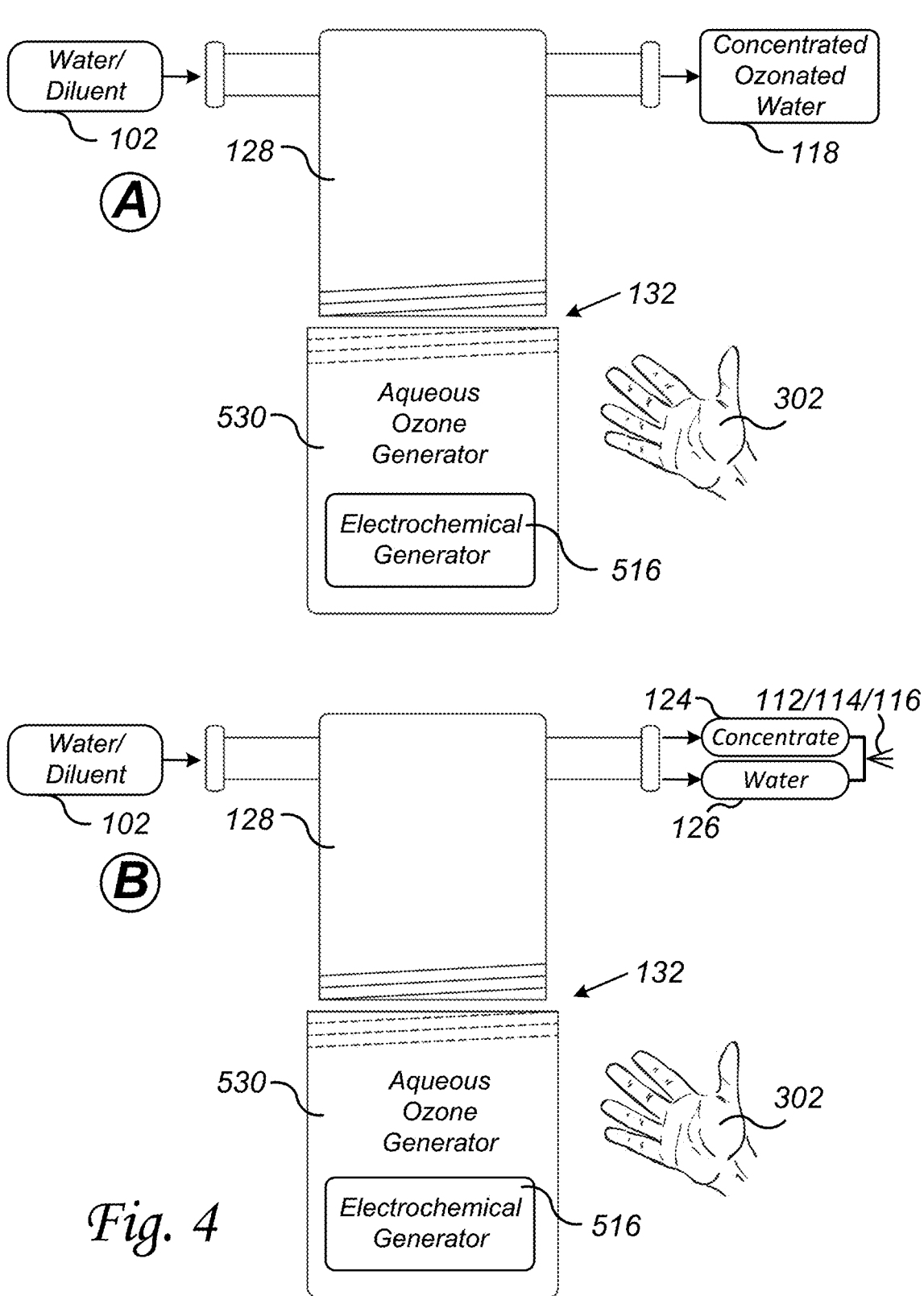
FIG. 4 illustrates one example of a plumbed housing interconnected with an aqueous ozone generator configured housing.

Referring to FIG. 4, there are illustrated examples of a plumbed housing 128 interconnected with an aqueous ozone generator 530. In an exemplary embodiment, aqueous ozone production involves electrolysis and an ion exchange material 534 which consumes certain components and materials during the process. Thus, when the service life of the aqueous ozone generator 530 and/or electrochemical generator 516 is over the generators 516/530 need to be replaced. To ease and speed generator 516/530 exchange by technician 302 a plumbed housing 128 can be permanently plumbed or otherwise fastened in place and the aqueous ozone generator 530 screwed 132 on to or otherwise fastened 132 in a removable manner to the plumbed housing 128. In this regard, the aqueous ozone generator 530 can be easily and quickly removed and exchanged for a new aqueous ozone generator 530 and electrochemical generator 516 when the aqueous ozone generator 530 and/or electrochemical generator 516 need to be replaced.

An advantage, in the present invention, is that once the plumbed housing 128 is installed and the liquid lines connected, the liquid lines don't need to be removed or disconnected to change the aqueous ozone generator 530. This saves technician 302 time, and cost, and reduces the chance of creating leaks in the system by having to disconnect/reconnect liquid carrying hoses.

Another advantage, in the present invention, is how the outflow of the assembled unit 128/530 can be configured. In this regard, in reference 'A' the assembled unit 128/530 can be configured to produce an ozonated concentrate liquid 118, or in reference 'B' and as better illustrated in at least FIG. 3 configured to produce an outflow of an ozonated concentrate stream 124 and a water stream 126. These streams 124/126 can be mixed at the point of departure or mixed in the air as they are sprayed from one or more of the nozzles 112/114/116 and as may be required and/or desired in a particular embodiment.

In an exemplary embodiment, in operation, a plumbed housing 128 is fastened in fluid communication pathways with the water source 102 and the ozonated concentrate liquid 118. An electrochemical generator 516 is integrated into the aqueous ozone generator 530. The electrochemical generator 516 comprises an ion exchange material 534. The aqueous ozone generator 530 is interchangeable and removably fastened to the plumbed housing 128.

In an exemplary embodiment, an electrochemical generator 516 can be integrated into the aqueous ozone generator 530. The electrochemical generator comprises an ion exchange material 534. A computing device 732, operated by technician 302, can data communicate the test ozone concentration to a remote data processing resource 702, and receive from the remote data processing resource 702, by way of the computing device 732 a plurality of aqueous ozone generator service life data that corresponds to the remaining service life 826 of the electrochemical generator 516.

Referring to FIG. 5, there are illustrated examples of a ratiometric mixer 106/108/110. In an exemplary embodiment, in reference 'A', mixing can be done with a fixed orifice type manifold 140 where each orifice 316/318 is a different diameter creating the desired ratio of water 126 and ozonated concentrate liquid 124 resulting in a single outflow 134 at the desired ozone concentration to spray nozzles 112/114/116.

Alternatively, in reference 'B' and with reference to at least FIG. 7, a fixed orifice type manifold 140 can have the same size orifices 320, and pumps/valves 528/532 can be used to dispense water 126 and ozonated concentrate liquid 124 under control 414/416 to create the desired ratio of water and ozonated concentrate liquid to spray 112/114/116. An advantage of using pumps 528/532 and control system 500 timing 414/416 is that the concentration of the ozone water mixture can be dynamically changed. In this regard, as the floor cleaning machine 202 speeds up or slows down, and for other reasons and situations, the concentration of the ozone water mixtures through nozzles 106/108/110 can be changed by adjusting the pulse width timing 414/416 that operates the pumps 528/532. Including stopping the pulse width generation to stop mixing and spraying the ozone water mixtures through nozzles 106/108/110.

Figure 6:
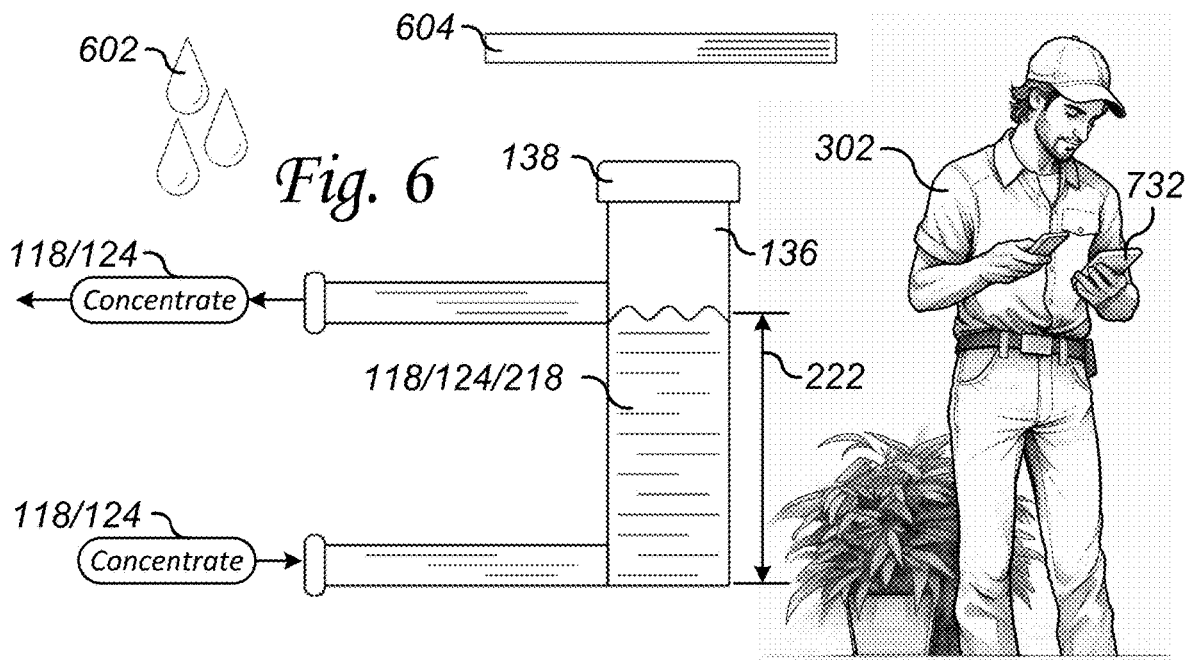
FIG. 6 illustrates one example of a fixed-volume inspection chamber.

Referring to FIG. 6, there is illustrated one example of a fixed-volume inspection chamber 136. In an exemplary embodiment, a fixed-volume inspection chamber 136 receives a continuous flow and maintains a fixed-volume portion 222 of the ozonated concentrate liquid 118/124, or other ozonated flow. Other ozonated flow can include the post-hygienic ozone disinfection solution, the midst-hygienic ozone disinfection solution, the post-hygienic ozone disinfection solution, or other ozonated solutions. The amount 218 of the fixed-volume is predetermined by test requirements of an ozone concentration test implement 602/604/606. Such amount 218 can be in the range of 200 milliliters (ml), or other amount as may be required and/or desired in a particular embodiment.

In a plurality of exemplary embodiments, more than one of the fixed-volume inspection chambers 136 can be used in an embodiment. In this regard, the fixed-volume inspection chambers 136 can incorporated at several places throughout the system 100 so that dissolved ozone concentrations can be checked. Such places can include ozonated concentrate liquid 118 lines, concentrate 124 lines, lines into or out of mixers 106/108/110, lines into nozzles 112/114/116, or other places throughout system 100 as may be required and/or desired in a particular embodiment.

In operation, the ozone concentration test implement 602/604/606 can include an ozone concentration test strip 604, an ozone concentration test drops 602, or an ozone concentration test device 606 to test for dissolved ozone, or other types and/or kinds of ozone concentration test implement. The ozone concentration test implements 602/604/606 can be manually used by technician 302 to determine a test ozone concentration of the ozonated concentrate liquid 118/124 by inserting the ozone concentration implement 602/604/606 into the fixed-volume inspection chamber 136 and then reading the test ozone concentration of ozonated concentrate liquid within.

For disclosure purposes, such ozone concentration test strip 604 can be SENSAFE type or brand, MACHERY-NAGEL type or brand, or other suitable types or brands. Such ozone concentration test drops 602 can be CHEMET-RICS type or brand, or other suitable types or brands.

In an exemplary embodiment, where access to the ozonated concentrate liquid 118/124 within the fixed-volume inspection chamber 136 is required an inspection chamber lid 138 can be configured to be open and closable as required and/or desired in a particular embodiment.

In an exemplary embodiment, the floor cleaning machine 202 comprises a cleaning mechanism 220. The floor cleaning machine 202 is capable of traversing a floor surface 204 entering a pre-hygienic zone 204A prior to cleaning, cleaning within a midst-hygienic zone 204B for a cleaning period midst-T2 208 by way of the cleaning mechanism 220, and moving away from the midst-hygienic zone 204B creating a post-hygienic zone 204C.

An aqueous ozone generator 530 receives a portion of the water source 102 and generates from the water source 102 an ozonated concentrate liquid 116. The aqueous ozone generator 530 comprises a plumbed housing 128 that is fastened in fluid communication pathways with the water source 102, the ozonated concentrate liquid 118, and an electrochemical generator 516. The electrochemical generator 516 comprises an ion exchange material 534. The electrochemical generator 516 is interchangeable and removably fastened to the plumbed housing 128.

A fixed-volume inspection chamber 136 receives a continuous flow and maintains a fixed-volume portion 222 of the ozonated concentrate liquid 118 or the post-hygienic ozone disinfection solution. The amount of the fixed-volume portion 222 is predetermined by the test requirements of an ozone concentration test implement 602/604/604.

In a plurality of exemplary embodiments, more than one of the fixed-volume inspection chambers 136 can be used in an embodiment. In this regard, the fixed-volume inspection chambers 136 can incorporated at several places throughout the system 100 so that dissolved ozone concentrations can be checked. Such places can include ozonated concentrate liquid 118 lines, concentrate 124 lines, lines into or out of mixers 106/108/110, lines into nozzles 112/114/116, or other places throughout system 100 as may be required and/or desired in a particular embodiment.

A post-hygienic mixer 110 receives and ratiometrically blends a portion of the ozonated concentrate liquid 118 and a portion of the water source 102 to form a post-hygienic ozone disinfection solution having a predetermined post-hygienic ozone treatment concentration which is less than ozone concentration of the ozonated concentrate liquid 118. The predetermined post-hygienic ozone treatment concentration is selected to achieve sterilization of the floor surface 204 within a post-hygienic treatment time post-T3 210. The post-hygienic treatment time post-T3 210 is greater than the cleaning period midst-T2 208.

A post-hygienic nozzle 116 is mounted on the floor cleaning machine 202 proximate to the transition 214 between the midst-hygienic zone 204B and the post-hygienic zone 204C. The post-hygienic nozzle 116 directs the spray of the post-hygienic ozone disinfection solution onto the post-hygienic zone 204C portion of the floor surface 204. In operation, cleaning within the midst-hygienic zone 204B removes debris from the floor surface 204, allowing the post-hygienic ozone disinfection solution sprayed on the post-hygienic zone 204B to contact the floor surface 204 in an unencumbered by debris manner for at least the post-hygienic treatment time post-T3 210 absent agitation or removal by the floor cleaning machine 202 improving disinfection of the floor surface 204.

In operation, the ozone concentration test implement 602/604/606 can include an ozone concentration test strip 604, an ozone concentration test drops 602, an ozone concentration test device 606 to test for dissolved ozone, or other suitable ozone concentration test implement. The ozone concentration test implements 602/604/606 are manually used by technician 302 to determine a test ozone concentration of the ozonated concentrate liquid or the post-hygienic ozone disinfection solution within the fixed-volume inspection chamber 136 by inserting the ozone concentration implement 602/604/606 into the fixed-volume inspection chamber 136 and then reading the test ozone concentration of ozonated concentrate or the post-hygienic ozone disinfection solution within.

Figure 10:
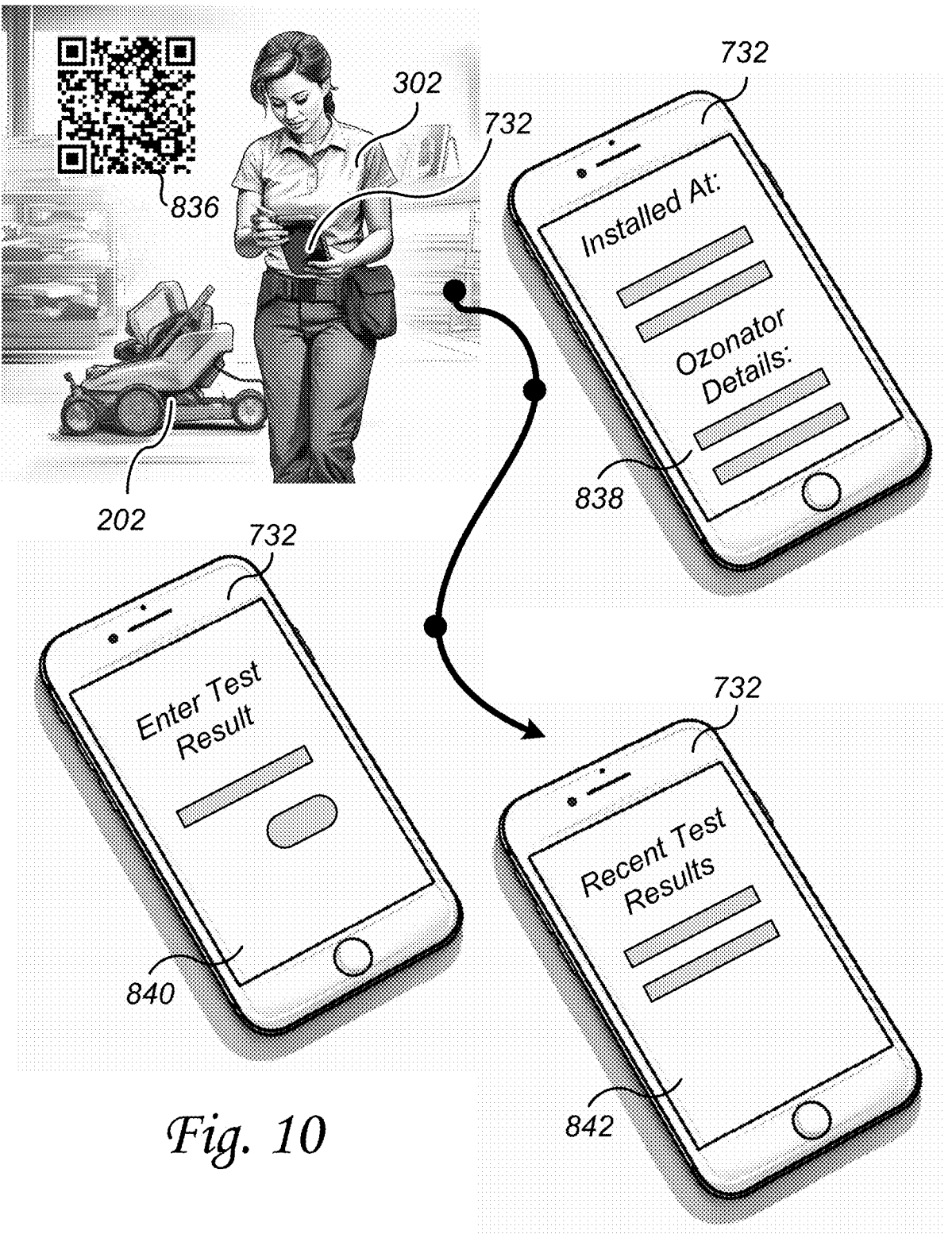
FIG. 10 illustrates one example of a technician's use of a software application.

In an exemplary embodiment and with reference to at least FIG. 10, a computing device 732, operated by technician 302, data communicates the test ozone concentration to a remote data processing resource 702, and receives from the remote data processing resource 702, by way of the computing device 732 a plurality of aqueous ozone generator service life data that corresponds to the remaining service life 826 of the electrochemical generator 516.

In an exemplary embodiment, in operation, technician 302 can scan a QR code 836 or other suitable identifier to identify the specific aqueous ozone disinfection system 100 installed in the floor cleaning machine 202.

In screenshot 832, the specific aqueous ozone disinfection system 100 identification can be data communicated to the remote data processing resource 702 and received in return from the remote data processing resource 702 data related to where the specific aqueous ozone disinfection system 100 is installed, detailed information about the specific aqueous ozone disinfection system 100, and other relevant information, as may be required and/or desired in a particular embodiment.

In screenshot 840, technician 302 can enter the test ozone concentration reading just taken and data communicate the test ozone concentration reading to the remote data processing resource 702 where the test ozone concentration reading can be recorded.

In screenshot 842, received from the remote data processing resource is a plurality of aqueous ozone generator service life data related to specific aqueous ozone disinfection system 100. Such plurality of aqueous ozone generator service life data can comprise prior test results (time/date, ozone concentration, other data), the technicians who made those prior readings, an estimation of the remaining service life 826, maintenance information, service information, warning or alerts, and other relevant information, as may be required and/or desired in a particular embodiment.

In an exemplary embodiment, technician 302 can use an ozone sensor that is attached either temporarily or permanently to the control system 500. In this regard, in operation, a control system 500 can comprise a microcontroller 504, a memory 504, an ozone sensor 522 (attached temporarily to make a reading or permanently where test ozone readings can be initiated automatically and/or remotely), and a communication interface 508. The microcontroller 502 is operationally related to the memory 504, the ozone sensor 522, and the communication interface 508.

The memory 504 is encoded with instructions that when executed by the microcontroller 502 perform the steps of recording, by way of the ozone sensor 522, a test ozone concentration of the ozonated concentrate liquid or the post-hygienic ozone disinfection solution. By way of the communication interface, the test ozone concentration can be data communicated to a remote data processing resource 702. Confirmation of the recording of the test result by the remote data processing resource 702 can be the receiving, by way of the communication interface 508 of a plurality of aqueous ozone generator service life data. Such plurality of aqueous ozone generator service life data can comprise prior test results (time/date, ozone concentration, other data), the technicians who made those prior readings, an estimation of the remaining service life 826, maintenance information, service information, warning or alerts, and other relevant information, as may be required and/or desired in a particular embodiment.

Referring to FIG. 7, there is illustrated one example of mixing pulse sequence 400 by way of transitioning between pump/valve 528/532 activation pulses. The mixer pulse sequence 400 can be represented as a square wave 402/404 that indicated a time period 418 that an electronic pump/valve 528B-D/532A-C is energized 'ON' or 'OPEN' 410/412 to allow water 102 or ozonated concentrate liquid 118 to flow or in standby 'OFF' or "CLOSED" abating water 102 or ozonated concentrate liquid 118 flow.

In an exemplary embodiment, the mixing pulse sequence 400 is one or more of the pump/valves 528B-D/532A-B being energized and/or otherwise 'OPENED' for a predetermined amount of time to allow water 102 or ozonated concentrate liquid 118 to enter the mixer 106/108/110. A longer 'OPEN' predetermined amount of time allows more of the specific water 102 or ozonated concentrate liquid 118 to enter the mixer 106/108/110. By predetermining an amount of time for each of the water 102 or ozonated concentrate liquid 118, the water 102 or ozonated concentrate liquid 118 amounts can be blended to form the pre-hygienic ozone disinfection solution and sprayed from nozzle 112, the midst-hygienic ozone disinfection solution and sprayed from nozzle 114, or the post-hygienic ozone disinfection solution and sprayed from nozzle 116.

As an example, with pumps/valves 528/532 providing comparable performance, a ratio of one part ozonated concentrate liquid 118, to two parts water source 102 can be achieved by 'OPENING' electronic pump/valve 528B, 528C, or 528D that controls water source 102 flow into the mixers 106/108/110 for twice the amount of time as the electronic pump/valve 532A, 532B, or 532C that controls the flow of the ozonate concentrate liquid 118 into the mixer 106/108/110.

In an exemplary embodiment, in reference 'A' 414 initially electronic pump/valve 532A, 532B, or 532C is energized allowing water source 102 to enter the mixer chamber 106, 108, or 110 for a predetermined time period 410. The mixer pulse sequence 400 then continues in reference 'B' 416 by energizing electronic pump/valve 528B, 528C, or 528D allowing the ozonated concentrate liquid 118 to enter the mixer chamber 106, 108, or 110 for a predetermined time period 412.

The mixer pulse sequence 400 repeats as needed. Each mixer pulse sequence 400 ratiometrically blends the water source 102 and the ozonated concentrate liquid 118 by injecting them in predetermined quantities into the mixer 106, 108, or 110.

In an exemplary embodiment, a pressure equalization pause 406 can be inserted between transition signals 402/404. In this regard, each time a pump/valve 528B-D/532A-C is turned 'OFF' or 'CLOSED' a pressure equalization pause 406 can occur before turning the next pump/valve 528B-D/532A-C 'ON' or 'OPENING'. This pressure equalization pause 406 allows pressures in the coupled lines to the pump/valve 528B-D/532A-C and system in general to stabilize so that when the next pump/valve 528B-D/532A-C is turned 'ON' or 'OPENED' the pressure is the same as prior sequence cycle and the flow during the timing sequence is predictable and accurate each sequence cycle for the water and the ozonated concentrate liquid 118 being inject into the mixers 106, 108, or 110.

In an exemplary embodiment, a water pump 528D can be configured to pump the water source 102 into the post-hygienic mixer 110. A concentrate pump 532C is configured to pump ozonated concentrate 118/124 into the post-hygienic mixer 110. A control system 500 comprises a microcontroller 502, a memory 504, the water pump 528D, and the concentrate pump 532C. The microcontroller 502 is operationally related to the memory 504, the water pump 528D, and the concentrate pump 532C.

The memory 504 can be encoded with instructions that when executed by the microcontroller 502 perform the steps of mixing the post-hygienic ozone disinfection solution in the predetermined post-hygienic ozone treatment concentration by transitioning between activating the water pump 528D for a water pulse 402 width period 410, allowing the water source 102 to flow into the post-hygienic mixer 110 during the water pulse 402 width period 410. And, activating the concentrate pump 532C for a concentrate pulse 404 width period 412, allowing the ozonated concentrate liquid 118/124 to flow into the post-hygienic mixer 110 during the concentrate pulse 404 width period 412. In operation, the water pulse 402 width period 410 and the concentrate pulse 404 width period 412 are selected to produce the post-hygienic ozone disinfection solution at the predetermined post-hygienic ozone treatment concentration.

In another exemplary embodiment, the memory 504 can be encoded with instructions that when executed by the microcontroller 502 perform the steps of mixing the midst-hygienic ozone disinfection solution in the predetermined midst-hygienic ozone treatment concentration by transitioning between activating the water pump 528C for a water pulse 402 width period 410, allowing the water source 102 to flow into the midst-hygienic mixer 108 during the water pulse 402 width period 410. And, activating the concentrate pump 532B for a concentrate pulse 404 width period 412, allowing the ozonated concentrate liquid 118/124 to flow into the midst-hygienic mixer 108 during the concentrate pulse 404 width period 412. In operation, the water pulse 402 width period 410 and the concentrate pulse 404 width period 412 are selected to produce the midst-hygienic ozone disinfection solution at the predetermined midst-hygienic ozone treatment concentration.

In an exemplary embodiment, the predetermined midst-hygienic ozone treatment concentration of the midst-hygienic ozone disinfection solution can be changed based on speed changes of the floor cleaning machine 202 along the floor surface 204. In operation, speed increases of the floor cleaning machine 202 can increase the predetermined midst-hygienic ozone treatment concentration since the midst-T2 208 is decreased, shortening disinfection time and speed decreases of the floor cleaning machine 202 can decrease the predetermined midst-hygienic ozone treatment concentration the midst-T2 208 is increased, lengthening disinfection time.

In another exemplary embodiment, the memory 504 can be encoded with instructions that when executed by the microcontroller 502 perform the steps of mixing the pre-hygienic ozone disinfection solution in the predetermined pre-hygienic ozone treatment concentration by transitioning between activating the water pump 528B for a water pulse 402 width period 410, allowing the water source 102 to flow into the pre-hygienic mixer 106 during the water pulse 402 width period 410. And, activating the concentrate pump 532A for a concentrate pulse 404 width period 412, allowing the ozonated concentrate liquid 118/124 to flow into the pre-hygienic mixer 106 during the concentrate pulse width 404 period 412. In operation, the water pulse 402 width period 410 and the concentrate pulse 404 width period 412 are selected to produce the pre-hygienic ozone disinfection solution at the predetermined pre-hygienic ozone treatment concentration.

In an exemplary embodiment, the predetermined pre-hygienic ozone treatment concentration of the pre-hygienic ozone disinfection solution can be changed based on speed changes of the floor cleaning machine 202 along the floor surface 204. In operation, speed increases of the floor cleaning machine 202 can increase the predetermined pre-hygienic ozone treatment concentration since the pre-T1 206 is decreased, shortening disinfection time and speed decreases of the floor cleaning machine 202 can decrease the predetermined pre-hygienic ozone treatment concentration the pre-T1 206 is increased, lengthening disinfection time.

Referring to FIG. 8, there is illustrated one example of a system and network diagram. In an exemplary embodiment, users of the platform and network can include technicians 302, administrators 304, or other authorized persons.

Each of the users uses computing devices 732A-C to data communicate over a global communication network 700 with one or more data processing resources 702. The computing devices 732A-C can be laptop computers, desktop computers, smartphones, tablets, or other types and kinds of computing devices, as may be required and/or desired in a particular embodiment. For disclosure purposes, computing devices 732A-C can be referred to as computing devices

732. Additionally, laptop and desktop types of computing devices 732 can be referred to as computing devices 712C, computing devices 732 such as smartphones can be referred to as computing devices 732B, and computing devices 732 such as tablets can be referred to as computing devices 732A. In operation, any of the users can use any of the types of computing devices 732A-C, without limitation to the type or kind of computing device 732, as may be required and/or desired in a particular embodiment. The global communication network 700 can be the Internet.

The computing devices 732 can comprise a microprocessor 704B/704C, a database 706B/706C, memory 208C, a communication interface 710B/710C, a display 712B/712C, and a plurality of general-purpose inputs and outputs (GPIO) 714B/714C.

Additionally, mobile type of computing device 732A/732B (tablets, smartphones, and others) can comprise a global positioning system (GPS) 716, and a microphone and/or camera 718.

In general, computing devices 232 can be configured with other functions and features, as may be required and/or desired in a particular embodiment.

In an exemplary embodiment, the microprocessor 704B is operationally related to database 706B, memory 708B, communication interface 710B, display 712B, and GPIO 714B

In an exemplary embodiment, the microprocessor 704C is operationally related to database 706C, memory 708C, communication interface 710C, display 712C, GPIO 714C, and if equipped with GPS 716, and microphone and/or camera 718. The computing devices 732 each rely on a suitable power source 720B/720C which can include a rechargeable battery, external power supply, or other types and/or kinds of power sources.

Microprocessor 704B/704C can be INTEL, ZILOG, MICROCHIP, AMD, ARM, and/or other types or kinds of microprocessors.

Database 706B/706C can be SQL, MYSQL, MARIADB, ORACLE, MS ACCESS, network-accessible storage, flat files, a combination thereof, or other types and kinds of databases.

Memory 708B/708C can be a combination of RAM, ROM, flash, hard drives, solid-state drives, USB flash drives, micro-SD cards, or other types of removable memory, and/or other types and kinds of memory.

The communication interfaces 710B/710C can be LAN, WAN, USB, Ethernet, RS232, RS485, serial, Wi-Fi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

Display 712B/712C can be a liquid crystal display (LCD), light emitting diode (LED), organic light emitting diode (OLED), or other types and kinds of displays.

The general-purpose inputs and outputs (GPIO) 714B/714C can be TTL, CMOS, MOSFET, transistors, buffers, relays, pushbuttons, switches, and/or other types and kinds of GPIO circuits. In an exemplary embodiment, some of the GPIO 214 lines can be used to drive a touch screen input, biometric input devices, keyboards, and/or types and kinds of computing device input devices.

Global positioning system (GPS) device 716 can be used to determine the geographic location of technician 302 and others who are carrying a computing device 732 equipped with a GPS 716. In this regard, such computing devices 732 are typically mobile computing devices such as tablets 732A, smartphones 732B, and other similar types and/or kinds of mobile computing devices 732.

Microphone and/or camera 718 can be used to record audio, and video, and take pictures. In this regard, users 304/306 can use their computing devices equipped with a microphone and/or camera 718 to make digital media records that can be selectively shared as appropriated including on social media and other digital media outlet locations.

With reference to FIG. 8, the data processing resource 702 can be a server, network storage device, or other types and kinds of data processing resources. Such data processing resources can be AMAZON WEB SERVICES (AWS), MICROSOFT AZURE, or other types and kinds of hosted data processing resource services. For disclosure purposes, a remote data processing resource 702 can also be referred to as server 702.

The data processing resource 702 can comprise a microprocessor 704A, a database 706A, memory 708A, and a communication interface 710A. The microprocessor 704A is operationally related to database 706A, memory 708A, and communication interface 710A.

The microprocessor 704A can be INTEL, ZILOG, MICROCHIP, AMD, ARM, and/or other types or kinds of microprocessors.

The database 706A can be SQL, MYSQL, MARIADB, ORACLE, MS ACCESS, network accessible storage, flat files, a combination thereof, or other types and kinds of databases.

The memory 708A can be a combination of RAM, ROM, flash, hard drives, solid-state drives, USB flash drives, micro-SD cards, or other types of removable memory, and/or other types and kinds of memory.

The communication interfaces 710A can be LAN, WAN, USB, Ethernet, RS232, RS485, serial, Wi-Fi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

Figure 9:
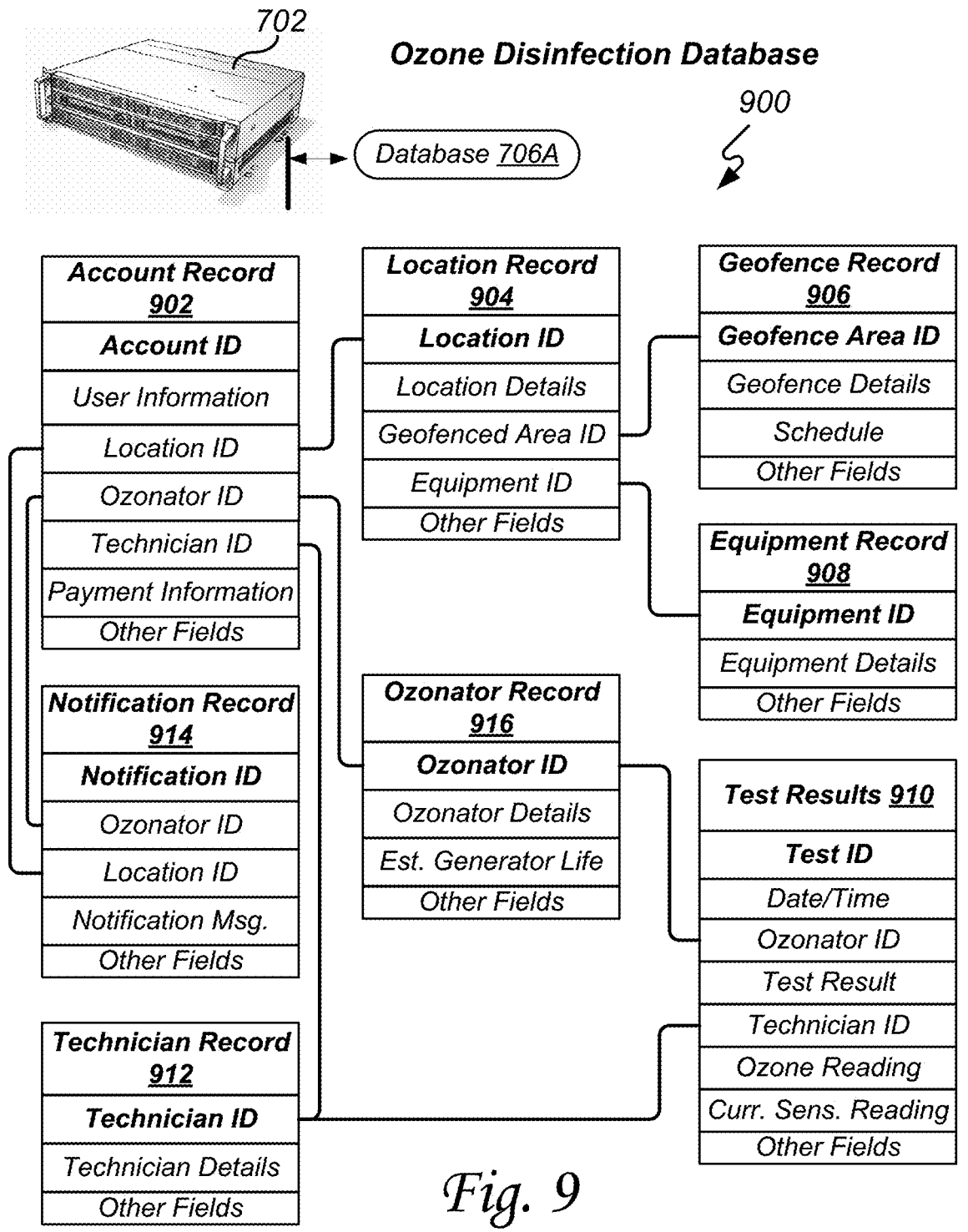
FIG. 9 illustrates one example of an ozone disinfection database structure.

Referring to FIG. 9, there is illustrated one example of an ozone disinfection database structure 900. In an exemplary embodiment, at least one database 706A/706B/706C can be implemented on at least one of the data processing resources 702 also referred to as server 702, or computing devices 732. In operation, one or more databases 706A/706B/706C can be accessed/created/managed/maintained as appropriate by more than one stakeholder. In this regard, in addition to system administrators and other authorized persons, other stakeholders can access/create/manage/maintain as appropriate.

In an exemplary embodiment, such databases 706A/706B/706C can be SQL, MYSQL, MARIADB, ORACLE, MS ACCESS, network-accessible storage, flat files, a combination thereof, or other types and kinds of databases.

In an exemplary embodiment, the ozone disinfection database 900 can reside on a remote data processing resource 702 in database 706A. In this regard, the ozone disinfection database 900 can comprise a series of tables, records, fields, and accounts that include account record 902, location record 904, geofence record 906, equipment record 908, test results 910, technician record 912, notification record 914, ozonator record 916, and/or other types or kinds of records as may be required and/or desired in a particular embodiment. The database structure illustrated in FIG. 9 also illustrates the relationship between the various tables.

In an exemplary embodiment, the data structure of account record 902 is illustrative and can be expanded and modified without particular limitation as needed and as appropriate to support the functionality and methods of the present invention and to support future functionality and methods of the present invention as it grows and evolves over time.

Referring to FIG. 11, there is illustrated one example of a floor plan 802 to monitor geofenced floor surfaces 804/806/808 that have been treated with the post-hygienic ozone disinfection solution. In an exemplary embodiment, by way of a global position system (GPS) 514 a disinfected post-hygienic zone GPS location 804/506/808 also referred to as geofenced floor surfaces 804/806/808 can be recorded when the post-hygienic ozone disinfection solution has been dispensed on the post-hygienic zone 204C. By way of the communication interface 508, the disinfected post-hygienic zone GPS location 804/806/808 can be data communicated to a remote data processing resource 702. In operation, the portion of floor surface 204 that has been treated with the post-hygienic ozone disinfection solution can be remotely monitored.

Additionally, in an exemplary embodiment, alerts 812/814 can be generated when for example the floor surface was not treated with a sufficiently high enough concentration of ozone to achieve adequate disinfection, areas of the floor surface were missed, or for other reasons as may be required and/or desired in a particular embodiment. Such alerts 812/814 can also be noted on reports 810.

In another exemplary embodiment, reports 810 can be generated to monitor, track, and summarize activities. Such reports 810 can include a plurality of aqueous ozone generator service life data, ozone concentration test results, geofenced floor surfaces 804/806/808 description, location, disinfection history, and other data as may be required and/or desired in a particular embodiment.

Figure 12:
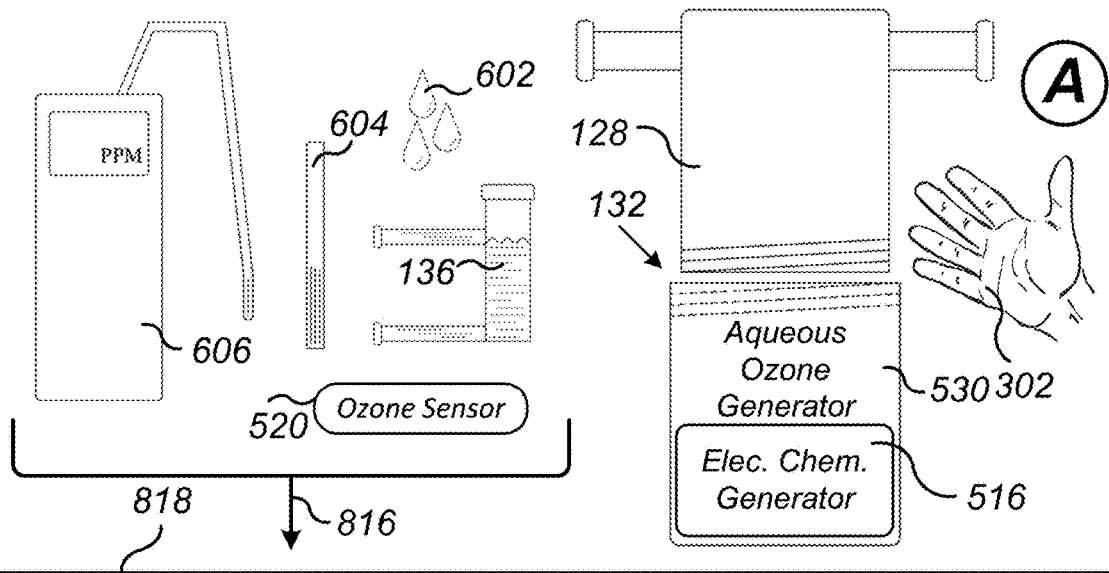
FIG. 12 illustrates one example of monitoring ozone concentration test results.
Figure 12:
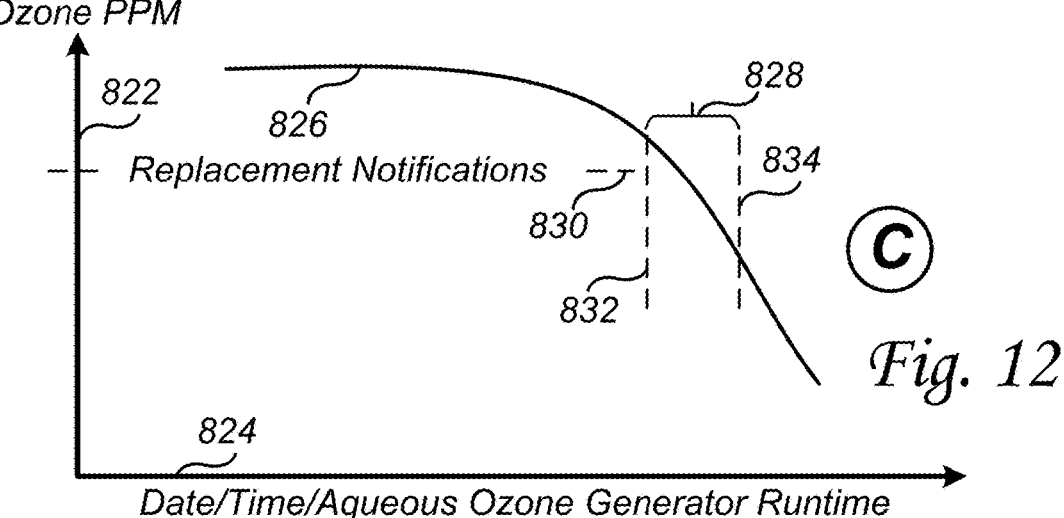

Referring to FIG. 12, there is illustrated one example of monitoring ozone concentration test results. In an exemplary embodiment in reference 'A', test ozone concentration of the ozonated concentrate liquid 118/124 or the post-hygienic ozone disinfection solution can be generated by way of a plurality of ozone concentration test implement that include ozone concentration test strips 604, ozone concentration test drops 602, ozone concentration test device 606, and ozone sensor 520.

In reference 'B', such ozone concentration test results 816 can be recorded on a remote data processing resource and used to generate reports 818 such reports can be tailored as needed and can be referred to as a plurality of aqueous ozone generator service life data. Such plurality of aqueous ozone generator service life data can comprise prior test results (time/date, ozone concentration, other data), the technicians who made those prior readings, an estimation of the remaining service life 826, maintenance information, service information, warning or alerts, and other relevant information, as may be required and/or desired in a particular embodiment.

An advantage, in the present invention, and with reference to 'C', is that by tracking ozone concentration 822 test results over time 824 the remaining service life 826 also referred to as the service life status of the electrochemical generator 516 and/or the aqueous ozone generator 530 can be determined or otherwise predicted. In this regard, components and materials within the electrochemical generator 516 and/or the aqueous ozone generator 530 degrade over time under normal use. A metric that changes as the efficiency of the electrochemical generator 516 and/or the aqueous ozone generator 530 degrade can be the amount of ozone produced and thus changes in ozone concentrations ppm can be observed over time. This present invention can establish a range 828 where ozone concentration test results above 832 are considered acceptable and ozone concentration test results 820 are below 834 are considered unacceptable. Appropriate electrochemical generator 516 and/or the aqueous ozone generator 530 replacement notifications 830 can be sent to technician 302 and/or the administrator. Such replacement notification can inform technician 302, and/or administrator 304 that the electrochemical generator 516 and/or the aqueous ozone generator 530 need to be serviced or replaced.

In the case that the ozone concentration test results indicated premature degradation of the electrochemical generator 516 and/or the aqueous ozone generator 530 before a normal life expectance, technician 302 and/or administrator 304 can be notified to check for water mineral scaling of the electrochemical generator 516 and/or the aqueous ozone generator 530 components and clean as appropriate. The ability of the present invention to detect mineral scaling which is cleanable can save the technician 302 and/or the administrator the cost of prematurely replacing the electrochemical generator 516 and/or the aqueous ozone generator 530.

In an exemplary embodiment, in operation, the service life status of the electrochemical generator 516 and/or the aqueous ozone generator 530 can be displayed on display 506/712B/712C. The service life status is based on the plurality of aqueous ozone generator service life data received from the remote data processing resource 702.

In an exemplary embodiment, in cases where the ozone concentration test results 826 are out of range 828 and/or are below 834 which is considered unacceptable, the floor cleaning machine 202 can be prevented from operating. In other words, if the plurality of aqueous ozone generator service life data indicates the aqueous ozone generator has reached the end of service life the floor cleaning machine can be prevented from working until the electrochemical generator 516 and/or aqueous ozone generator 530 is serviced or replaced.

Referring to FIG. 13, there is illustrated one example of a method of using an aqueous ozone floor disinfection system 100. In an exemplary embodiment, the method begins in step 1002 by operating, with the intent to clean a floor surface 204 with a floor cleaning machine 202. The floor cleaning machine 202 comprises a cleaning mechanism 220. The method then moves to step 1004.

In step 1004, the floor cleaning machine 202 traverses the floor surface 204, enters a pre-hygienic zone 204A prior to cleaning, cleans within a midst-hygienic zone 204B for a cleaning period midst-T2 by way of the cleaning mechanism 220, and moves away from the midst-hygienic zone 204B creating a post-hygienic zone 204C. The method then moves to step 1006.

In step 1006, an ozonated concentrate liquid 118 is created. An aqueous ozone generator 530 receives a portion of a water source 102 and generates from the water source 102 the ozonated concentrate liquid 118. The method then moves to step 1008.

In step 1008, a post-hygienic ozone disinfection solution is created at a predetermined post-hygienic ozone treatment concentration. A post-hygienic mixer 110 receives and ratiometrically blends a portion of the ozonated concentrate liquid 118 and a portion of the water source 102 to form the post-hygienic ozone disinfection solution having the predetermined post-hygienic ozone treatment concentration which is less than the ozone concentration of the ozonated concentrate liquid 118. The predetermined post-hygienic ozone treatment concentration is selected to achieve sterilization of the floor surface 204 within a post-hygienic treatment time post-T3 210. The post-hygienic treatment time post-T3 210 is greater than the cleaning period midst-T2 208. The method then moves to step 1010.

In step 1010, the post-hygienic zone 204C is disinfected. A post-hygienic nozzle 116 is mounted on the floor cleaning machine 202 proximate to the transition 214 between the midst-hygienic zone 204B and the post-hygienic zone 204C. The post-hygienic nozzle 116 directs the spray of the post-hygienic ozone disinfection solution onto the post-hygienic zone 204C portion of the floor surface 204. In operation, cleaning within the midst-hygienic zone 204B removes debris from the floor surface 204 allowing the post-hygienic ozone disinfection solution sprayed on the post-hygienic zone 204C to contact the floor surface 204 in an unencumbered by debris manner for at least the post-hygienic treatment time post-T3 210 absent agitation or removal by the floor cleaning machine 202 improving disinfection of the floor surface 204.

Referring to FIG. 14, there are illustrated exemplary embodiments that can be interchangeably used with the methods of the present invention.

In step 1102, the floor cleaning machine 202 can be prevented from operating if the plurality of aqueous ozone generator service life data indicates the aqueous ozone generator has reached the end of service life.

In step 1104, the service life status of the electrochemical generator 516 is displayed on the display 506/712B/712C. The service life status is based on the plurality of aqueous ozone generator service life data received from the remote data processing resource 702.

In step 1106, the service life of the aqueous ozone generator 530 can be verified by step 1108 of filling a fixed-volume inspection chamber 136. The fixed-volume inspection chamber 136 receives a continuous flow and maintains a fixed-volume portion 222 of the ozonated concentrate liquid 118/124 or the post-hygienic ozone disinfection solution. The amount of the fixed volume is predetermined by test requirements of an ozone concentration test implement 602/604/606. The ozone concentration test implement 602/604/606 includes an ozone concentration test strip 604, an ozone concentration test drops 602, an ozone concentration test device 606, or other suitable ozone concentration test implements. The method then moves to step 1110.

In step 1110, a test ozone concentration of the ozonated concentrate liquid or the post-hygienic ozone disinfection solution is determined, within the fixed-volume inspection chamber 136, by way of a technician 302 manually inserting the ozone concentration implement 602/604/606 into the fixed-volume inspection chamber 136 and then reading the test ozone concentration of ozonated concentrate 118/124 or the post-hygienic ozone disinfection solution within.

Referring to FIG. 15, there is illustrated exemplary embodiments that can be interchangeably used with the methods of the present invention.

In step 1112, the post-hygienic ozone disinfection solution is mixed in the predetermined post-hygienic ozone treatment concentration by transitioning between step 1114 of activating the water pump 528A for a water pulse 402 width period 410, allowing the water source 102 to flow into the post-hygienic mixer 110 during the water pulse 402 width period 410. And, step 1116, the concentrate pump 532C is activated for a concentrate pulse 404 width period 412, allowing the ozonated concentrate liquid 118/124 to flow into the post hygienic mixer 110 during the concentrate pulse 404 width period 412. In operation, the water pulse 402 width period 410 and the concentrate pulse 404 width period 412 are selected to produce the post-hygienic ozone disinfection solution at the predetermined post-hygienic ozone treatment concentration.

In step 1118, by way of the GPS 514, a disinfected post-hygienic zone GPS location is recorded when the post-hygienic ozone disinfection solution is being dispensed on the post-hygienic zone 204C. The method then moves to step 1120.

In step 1120, by way of the communication interface, the disinfected post-hygienic zone GPS location is data communicated to a remote data processing resource 702. In operation, the floor surfaces 204 that have been treated with the post-hygienic ozone disinfection solution can be remotely monitored.

In step 1122, the post-hygienic ozone disinfection solution can be dispensed by way of the post-hygienic pump 528, as better illustrated in at least FIG. 3 reference 'B', when the motion sensor 518 detects the floor cleaning machine 202 is moving in a manner that is creating the post-hygienic zone 204C.

In step 1124, by way of the ozone sensor 522, a test ozone concentration of the ozonated concentrate liquid or the post-hygienic ozone disinfection solution is recorded. The method then moves to step 1126.

In step 1126, by way of the communication interface 508, the test ozone concentration is data communicated to a remote data processing resource 702. The method then moves to step 1128.

In step 1128, from the remote data processing resource 702, by way of the communication interface 508 a plurality of aqueous ozone generator service life data is received.

The capabilities of the present invention can be implemented in software, firmware, hardware, or some combination thereof.

As one example, one or more aspects of the present invention can be included in an article of manufacture (e.g., one or more computer program products) having, for instance, computer-usable media. The media has embodied therein, for instance, computer-readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. An aqueous ozone floor disinfection system comprising;

a cleaning mechanism that is capable of traversing a floor surface and cleaning the floor surface;

an aqueous ozone generator that receives water and generates an ozonated concentrate liquid from the water;

a mixer that receives and ratiometrically blends a portion of the ozonated concentrate liquid with water to form an ozone disinfection solution at a desired ozone concentration level, the mixer changes the ozone concentration levels of the ozone disinfection solution based on speed that the cleaning mechanism traverses the floor; and a nozzle that sprays the ozone disinfection solution onto the floor surface after the floor surface has been cleaned by the cleaning mechanism.

2. The aqueous ozone floor disinfection system in accordance with claim 1, the aqueous ozone generator comprising:

a plumbed housing that is fastened in fluid communication pathways with a water source; and the aqueous ozone generator is interchangeable and removably fastened to the plumbed housing and contains an electrochemical generator comprising an ion exchange material.

3. The aqueous ozone floor disinfection system in accordance with claim 1, further comprising:

a fixed-volume inspection chamber that receives, prior to dispensing onto the floor surface, a continuous flow of a portion of the ozonated concentrate liquid or the ozone disinfection solution and continuously maintains a fixed volume of such liquid or solution that can be accessed for ozone concentration testing.

4. The aqueous ozone floor disinfection system in accordance with claim 1, further comprising:

a second mixer that receives and ratiometrically blends a portion of the ozonated concentrate liquid and a portion of water to form a second ozone disinfection solution at a second desired ozone concentration level; and a second nozzle that sprays the second ozone disinfection solution onto the floor surface while the floor surface is being cleaned by the cleaning mechanism.

5. The aqueous ozone floor disinfection system in accordance with claim 4, further comprising:

a third mixer that receives and ratiometrically blends portion of the ozonated concentrate liquid and portion of water to form a third ozone disinfection solution at a third desired ozone concentration level; and a third nozzle that sprays the third ozone disinfection solution onto the floor surface before the floor surface is cleaned by the cleaning mechanism.

6. The aqueous ozone floor disinfection system in accordance with claim 1, further comprising:

a pump is configured to control the egress of the ozone disinfection solution from the nozzle; and a control system, the control system comprises a microcontroller, a memory, the pump, and a motion sensor, the microcontroller is operationally related to the memory, the pump, and the motion sensor, the memory is encoded with instructions that when executed by the microcontroller dispenses the ozone disinfection solution by way of the pump when the motion sensor detects the cleaning mechanism is moving.

7. The aqueous ozone floor disinfection system in accordance with claim 1, further comprising:

a water pump that is configured to pump water into the mixer;

a concentrate pump that is configured to pump the ozonated concentrate liquid into the mixer; and a control system, the control system comprises a microcontroller, a memory, the water pump, and the concentrate pump, the microcontroller is operationally related to the memory, the water pump, and the concentrate pump, the memory is encoded with instructions that when executed by the microcontroller perform the steps of:

activating the water pump for a water pulse width period, allowing the water source to flow into the mixer during the water pulse width period;

activating the concentrate pump for a concentrate pulse width period, allowing the ozonated concentrate liquid to flow into the mixer during the concentrate pulse width period; and wherein the water pulse width period and the concentrate pulse width period are selected to produce the disinfection solution at the desired ozone concentration level.

8. The aqueous ozone floor disinfection system in accordance with claim 1, further comprising:

a control system, the control system comprises a microcontroller, a memory, an ozone sensor, and a communication interface, wherein the microcontroller is operationally related to the memory, the ozone sensor, and the communication interface, and the memory is encoded with instructions that when executed by the microcontroller perform the steps of:

recording, by way of the ozone sensor, a test ozone concentration of the ozonated concentrate liquid or the post-hygienic ozone disinfection solution;

communicating, by way of the communication interface, the test ozone concentration to a data processing resource; and receiving, from the data processing resource, by way of the communication interface aqueous ozone generator operation data.

9. The aqueous ozone floor disinfection system in accordance with claim 1, further comprising:

a microcontroller;

a memory encoded with instructions that when executed by the microcontroller perform the step of:

preventing the cleaning mechanism from operating if the aqueous ozone generator operation data indicates the aqueous ozone generator is not working properly.

10. The aqueous ozone floor disinfection system in accordance with claim 9, further comprising:

a display, the microcontroller is operationally related to the display, and the memory is encoded with instructions that when executed by the microcontroller perform the steps of:

displaying an operation status of an electrochemical generator on the display, the operation status is based on the aqueous ozone generator operation data received from the data processing resource, the aqueous ozone generator comprises the electrochemical generator.

11. A method of using the aqueous ozone floor disinfection system of claim 1, the method comprising the steps of:

operating the cleaning mechanism on the floor surface;

creating the ozonated concentrate liquid from water with the aqueous ozone generator;

creating the ozone disinfection solution at the desired concentration level with the mixer that receives and ratiometrically blends a portion of the ozonated concentrate liquid with water; and disinfecting the floor surface by spraying the ozone disinfection solution onto the floor surface with the nozzle after it has been cleaned by the cleaning mechanism.

12. The method in accordance with claim 11, further comprising the steps of:

filling a fixed-volume inspection chamber which receives a continuous flow and maintains a fixed-volume portion of the ozonated concentrate liquid or the ozone disinfection solution; and determining a test ozone concentration of the ozonated concentrate liquid or the ozone disinfection solution, within the fixed-volume inspection chamber, by way of manually inserting an ozone sensor into the fixed-volume inspection chamber.

13. The method in accordance with claim 11, further comprising the steps of:

recording, by way of an ozone sensor, a test ozone concentration of the ozonated concentrate liquid or the ozone disinfection solution;

communicating the test ozone concentration to a data processing resource; and receiving, from the data processing resource, aqueous ozone generator operation data.

14. The method in accordance with claim 13, further comprising the steps of:

preventing the cleaning mechanism from operating if the aqueous ozone generator operation data indicates the aqueous ozone generator is not working properly.

15. The method in accordance with claim 13, further comprising the steps of:

displaying an operationstatus of an electrochemical generator, the operation status is based on the aqueous ozone generator operation data received from the data processing resource, the aqueous ozone generator comprises the electrochemical generator.

16. The method in accordance with claim 11, further comprising the steps of:

recording, by way of the GPS, a disinfected zone's GPS location when the ozone disinfection solution is being dispensed; and communicating, by way of the communication interface, the disinfected zone's GPS location to a data processing resource.

17. An aqueous ozone floor disinfection system comprising;

a cleaning mechanism that is capable of traversing a floor surface and cleaning the floor surface;

an aqueous ozone generator that receives water and generates an ozonated concentrate liquid from the water;

a mixer that receives and ratiometrically blends a portion of the ozonated concentrate liquid with water to form an ozone disinfection solution at a desired ozone concentration level, the mixer changes the ozone concentration levels of the ozone disinfection solution based on speed that the cleaning mechanism traverses the floor;

a nozzle that sprays the ozone disinfection solution onto the floor surface after it has been cleaned by the cleaning mechanism;

a second mixer that receives and ratiometrically blends a portion of the ozonated concentrate liquid and a portion of water to form a second ozone disinfection solution at a second desired ozone concentration level; and a second nozzle that sprays the second ozone disinfection solution onto the floor surface while the floor surface is being cleaned by the cleaning mechanism.

18. A method of using the aqueous ozone floor disinfection system of claim 17, the method comprising the steps of:

operating the cleaning mechanism on the floor surface;

creating the ozonated concentrate liquid from water with the aqueous ozone generator;

creating the ozone disinfection solution at the desired concentration level with the mixer that receives and ratiometrically blends a portion of the ozonated concentrate liquid with water;

creating the second ozone disinfection solution at the second desired concentration level with the second mixer that receives and ratiometrically blends a portion of the ozonated concentrate liquid with water; and disinfecting the floor surface by spraying the ozone disinfection solution onto the floor surface with the nozzle after the floor surface has been cleaned by the cleaning mechanism, and spraying the second ozone disinfection solution onto the floor surface with the second nozzle while the floor surface is being cleaned by the cleaning mechanism.

19. An aqueous ozone floor disinfection system comprising;

a cleaning mechanism that is capable of traversing a floor surface and cleaning the floor surface;

an aqueous ozone generator that receives water and generates an ozonated concentrate liquid from the water with ozone purity levels of at least 20%;

a mixer that receives and ratiometrically blends a portion of the ozonated concentrate liquid with water to form an ozone disinfection solution at a desired ozone concentration level;

a nozzle that sprays the ozone disinfection solution onto the floor surface;

a second mixer that receives and ratiometrically blends portion of the ozonated concentrate liquid and portion of water to form a second ozone disinfection solution at a second desired ozone concentration level;

a second nozzle that sprays the second ozone disinfection solution onto the floor surface before it is cleaned by the cleaning mechanism.

20. A method of using the aqueous ozone floor disinfection system of claim 19, the method comprising the steps of:

operating the cleaning mechanism on the floor surface;

creating the ozonated concentrate liquid from water with the aqueous ozone generator;

creating the ozone disinfection solution at the desired concentration level with the mixer that receives and ratiometrically blends a portion of the ozonated concentrate liquid with water;

creating the second ozone disinfection solution at the second desired concentration level with the second mixer that receives and ratiometrically blends a portion of the ozonated concentrate liquid with water; and disinfecting the floor surface by spraying the ozone disinfection solution onto the floor surface with the nozzle after the floor surface has been cleaned by the cleaning mechanism, and spraying the second ozone disinfection solution onto the floor surface with the second nozzle before the floor surface has been cleaned by the cleaning mechanism.

\* \* \* \* \*